(12) United States Patent
Welt et al.

(10) Patent No.: US 6,291,235 B1
(45) Date of Patent: Sep. 18, 2001

(54) ISOLATED NUCLEIC ACID WHICH ENCODES PROTEIN WHICH BINDS TO A33 ANTIBODY

(75) Inventors: Sydney Welt, New York, NY (US); Sara White; Cameron Johnstone, both of Melbourne (AU); Lloyd J Old; Gerd Ritter, both of New York, NY (US); Bruno Catimel, Melbourne (AU); Hong Ji, Melbourne (AU); Antony Burgess, Melbourne (AU); Joan Heath, Melbourne (AU); Richard J Simpson, Melbourne (AU); Edouard Nice, Melbourne (AU); R. L Moritz, Melbourne (AU)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/068,051
(22) PCT Filed: Aug. 5, 1996
(86) PCT No.: PCT/US96/12699
  § 371 Date: Dec. 12, 1998
  § 102(e) Date: Dec. 12, 1998
(87) PCT Pub. No.: WO97/08189
  PCT Pub. Date: Mar. 6, 1997

Related U.S. Application Data

(63) Continuation-in-part of application No. 08/597,495, filed on Feb. 2, 1996, now Pat. No. 5,712,369, which is a continuation of application No. 08/511,876, filed on Aug. 4, 1995, now abandoned.

(51) Int. Cl.$^7$ ............ C12N 15/63; C12N 15/85; C12N 15/86; C07H 21/04
(52) U.S. Cl. ............ 435/320.1; 435/325; 536/23.1; 536/23.5
(58) Field of Search ............... 435/320.1, 325; 536/23.1, 23.5

(56) References Cited

PUBLICATIONS

Welt et al., J. Clin. Oncol. vol. 12, pp 1561–1571, 1994.*
King et al., B. J. Cancer, vol. 72, pp 1364–1372, 1995.*
Daghighian et al, J. Nucl. Med. vol. 37, pp 1052–1057, 1996.*

\* cited by examiner

*Primary Examiner*—W. Gary Jones
*Assistant Examiner*—Jehanne Souaya
(74) *Attorney, Agent, or Firm*—Fulbright & Jaworski, LLP

(57) ABSTRACT

This invention relates to isolated proteins and to peptides which are found on the surface of colon cells and colon cancer cells, as well as to nucleic acid molecules encoding said protein and peptides. The protein and peptides bind to tumor associated antibodies, such as mAb 33. The monomeric protein has a molecular weight of about 43 kD as determined by SDS gel electrophoresis under non-reducing conditions. In addition, this invention relates to the use of said nucleic acid molecules, protein, in monomeric or multimeric form, and to antibodies to said peptides in diagnostic, screening and therapeutic methods. This invention further relates to antibodies specific for said protein, in monomeric or multimeric form, and to antibodies to said peptides.

6 Claims, 20 Drawing Sheets

α-actin Mab

A33 Mab

FIG. 12

| Sample | Sequence | | Reference |
|---|---|---|---|
| 1. N-terminal | ISVETPQDVLRASQGKSVTLPCTYHTSTSSDREGLIQWDKL | (SEQ ID NO: 4) | HP-414 |
| 2. D-1 | DVLRASQGKSVTLPCTYHTSTSSREGLIQW | (SEQ ID NO: 5) | HP-463 |
| 3. D-2 | DKLLLTHTERVVIWPFSNKNYIHGELYKNRVSISNNAEQ | (SEQ ID NO: 6) | HP-462 |
| 4. D-3 | ELYKNRVSISNNAEQ | (SEQ ID NO: 7) | HP-461 |
| 5. D-4 | DXGTYECSVSLM | (SEQ ID NO: 8) | HP-466 |
| 6. Pc-1 | IQLTCQSKEGSPTPQY | (SEQ ID NO: 9) | HP-467 |
| 7. Pc-2 | LVLVPPSKPECGIEGEETIIGN | (SEQ ID NO: 10) | HP-468 |
| 8. P-1 | ILNQGQPLAQPASGEPV | (SEQ ID NO: 11) | HP-464 |
| 9. T-1 | EAYEEPPEQLR | (SEQ ID NO: 2) | HP-379 |
| 10. T-2 | VVIWPFSNK | (SEQ ID NO: 3) | HP-385 |

Note: 1 Peptide nomenclature: D, Asp-N-endoproteinase, t, trypsin, P, pepsin, Pc, peptides recovered from core material following therolysin/pepsin/Asp-N treatment of A33 antigen.
2 Pepetide D-4; residue X is considered an N-gylcosylated asparagine (motif: NXT); peptide mapping reveals that the cysteines in D-4 and the N-terminal sequence are connected via a disulphide bond.
3 Peptide D-1 is contained within the N-terminal sequence; peptides D-3 and T-2 are contained within peptide D-2.
4 The presence of at least one glycosylated site would indicate that the molecular weight of th A33 antigen is much lower than that observed on SDS-PAGE.

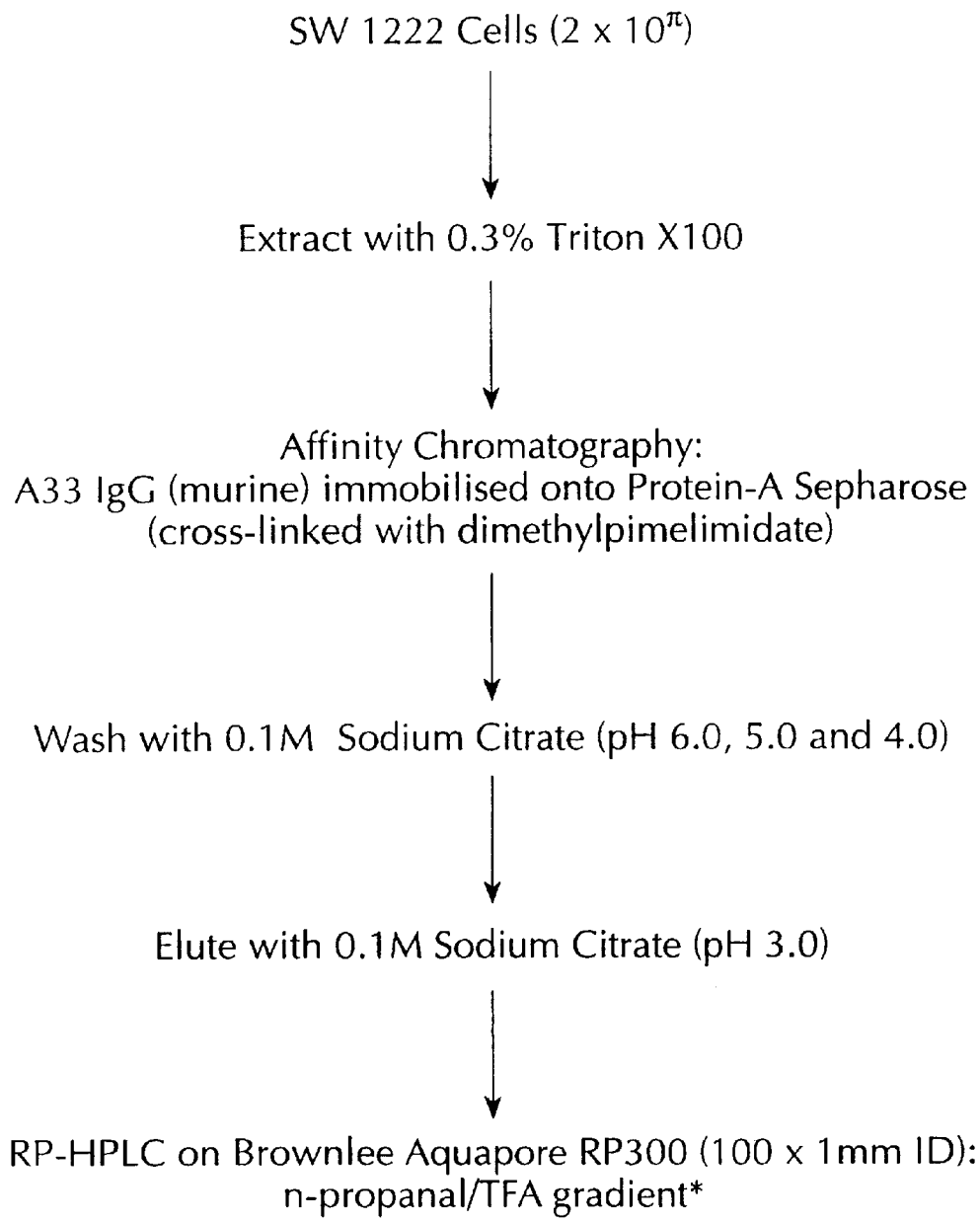

FIG. 16A

```
         10        20        30        40
GGGACTCCAGTTGGGCCAGGCCAGAAGCTGCTGTAGCTTT    40
AACCAGACAGCTCAGACCTCTATGGAGGCTGCCAGTGACA    80
GGTTAGGTTTAGGGCAGAGAAGAAGCAAGACCATGGTGGG   120
GAAGATGTGGCCTGTGTTGTGGACACTCTGTGCAGTCAGG   160
GTGACCGTCGATGCCATCTCTGTGGAACTCCGCAGGACG    200
        210       220       230       240
TTCTTCGGGCTTCGCAGGGAAaGAGTGTCACCCTGCCCTG   240
CACCTACCACACTTCCACCTCCAGTCGAGAGGGACTTATT   280
CAATGGGATAAGCTCCTCCTCACTCATACGGAAAGGGTGG   320
TCATCTGGCCGTTTTCAAACAAAAACTACATCCATGGTGA   360
GCTTTATAAGAATCGCGTCAGCATATCCAACAATGCTGAG   400
        410       420       430       440
CAGTCCGATGCCTCCATCACCATTGATCAGCTGACCATGG   440
CTGACAACGGCACCTACGAGTGTTCTGTCTCGCTGATGTC   480
AGACCTGGAGGGCAACACCAAGTCACGTGTCCGCCTGTTG   520
GTCCTCGTGCCACCCTCCAAACCAGAATGCGGCATCGAGG   560
GAGAGACCATAATTGGGAACAACATCCAGCTGACCTGCCA   600
        610       620       630       640
ATCAAAGGAGGGCTCACCAACCCCTCAGTACAGCTGGAAG   640
AGGTACAACATCCTGAATCAGGAGCAGCCCCTGGCCCAGC   680
CAGCCTCAGGTCAGCCTGTCTCCCTGAAGAATATCTCCAC   720
AGACACATCGGGTTACTACATCTGTACCTCCAGCAATGAG   760
GAGGGGACGCAGTTCTGCAACATCACGGTGGCCGTCACAT   800
        810       820       830       840
CTCCCTCCATGAACGTGGCCCTGTATGTGGGCATCGCGGT   840
GGGCGTGGTTGCAGCCCTCATTATCATTGGCATCATCATC   880
TACTGCTGCTGCTGCCGAGGGAAGGACGACAACACTGAAG   920
ACAAGGAGGATGCAAGGCCGAACCGGGAAGCCTATGAGGA   960
GCCACCAGAGCAGCTAAGAGAACTTTCCAGAGAGGGAG   1000
       1010      1020      1030      1040
GAGGAGGATGACTACAGGCAAGAAGAGCAGAGGAGCACTG   1040
GGCGTGAATCCCCGGACCACCTCGACCAGTGACAGGCCAG   1080
CAGCAGAGGGCGGCGGAGGAAGGGTTAGGGGTTCATTCTC   1120
CCGCTTCCTGGCCTCCCTTCTCCTTTCTAAGCCCTGTTCT   1160
CCTGTCCCTCCATCCCAGACATTGATGGGGACATTTCTTC   1200
```

FIG. 16B

```
           1210      1220      1230      1240
CCCAGTGTCAGCTGTGGGGAACATGGCTGGCCTGGTAAGG 1240
GGGTCCCTGTGCTGATCCTGCTGACCTCACTGTCCTGTGA 1280
AGTAACCCCTCCTGGCTGTGACACCTGGTGCGGGCCTGGC 1320
CCTCACTCAAGACCAGGCTGCAGCCTCCACTTCCCTCGTA 1360
GTTGGCAGGAGCTCCTGGAAGCACAGCGCTGAGCATGGGG 1400
           1410      1420      1430      1440
CGCTCCCACTCAGAACTCTCCAGGGAGGCGATGCCAGCCT 1440
TGGGGGGTGGGGGCTGTCCTGCTCACCTGTGTGCCCAGCA 1480
CCTGGAGGGGCACCAGGTGGAGGGTTTGCACTCCACACAT 1520
CTTTCTTGAATGAATGAAAGAATAAGTGAGTATGCTTGGG 1560
CCCTGCATTGGCCTGGCCTCCAGCTCCCACTCCCTTTCCA 1600
           1610      1620      1630      1640
ACCTCACTTCCCGTAGCTGCCAGTATGTTCCAAACCCTCC 1640
TGGGAAGGCCACCTCCCACTCCTGCTGCACAGGCCCTGGG 1680
GAGCTTTTGCCCACACACTTTCCATCTCTGCCTGTCAATA 1720
TCGTACCTGTCCCTCCAGGCCCATCTCAAATCACAAGGAT 1760
TTCTCTAACCCTATCCTAATTGTCCACATACGTGGAAACA 1800
           1810      1820      1830      1840
ATCCTGTTACTCTGTCCCACGTCCAATCATGGGCCACAAG 1840
GCACAGTCTTCTGAGCGAGTGCTCTCACTGTATTAGAGCG 1880
CCAGCTCCTTGGGGCAGGGCCTGGGCCTCATGGCTTTTGC 1920
TTTCCCTGAAGCCCTAGTAGCTGGCGCCCATCCTAGTGGG 1960
CACTTAAGCTTAATTGGGGAAACTGCTTTGATTGGTTGTG 2000
           2010      2020      2030      2040
CCTTCCCTTCTCTGGTCTCCTTGAGATGATCGTAGACACA 2040
GGGATGATTCCCACCCAAACCCACGTATTCATTCAGTGAG 2080
TTAAACACGAATTGATTTAAAGTGAACACACACAAGGGAG 2120
CTTGCTTGCAGATGGTCTGAGTTCTTGTGTCCTGGTAATT 2160
CCTCTCCAGGCCAGAATAATTGGCATGTCTCCTCAACCCA 2200
           2210      2220      2230      2240
CATGGGGTTCCTGGTTGTTCCTGCATCCCGATACCTCAGC 2240
CCTGGCCCTGCCCAGCCCATTTGGGCTCTGGTTTTCTGGT 2280
GGGNCTGTCCTGCTGCCCTCCCACNAGCCTCCTTCTGTTT 2320
GTCGAGCATTTCTTCTACTCTTGAGAGCTCAGGCAGCGTT 2360
AGGGCTGCTTAGGTCTCATGGACCAGTGGCTGGTCTCACC 2400
           2410      2420      2430      2440
CAACTGCAGTTTACTATTGCTATCTTTTCTGGATGATCAG 2440
AAAAATAATTCCATAAATCTATTGTCTACTTGCGATTTTT 2480
TAAAAAATGTATATTTTTATATATATTGTTAAATCCTTTG 2520
CTTCATTCCAAATGCTTTCAGTAATAATAAAATTGTGGGT 2560
GGAAA 2565
```

FIG. 17

```
Human: MVGKMWPVLWTLCAVRVTVDAISVETPQDVLRASQGKSVTLPCTYHTSTSSREG
Mouse:       LGKAGSVVWMLCAIWAADALTVETTQDILRAARGRSVTLPCTYNTYVSDREG LIQWDKLLLTHTERVVIWPFSNKNYIHGELYKNRVSISNNAEQSDASITIDQLT
FIQWDKLLRSQTERVVTWNFVTKKYIYGNRYENRVRVSNDAELSNASITIDQLT MADNGTYECSVSLMSDLEGNTKSRVRLLVLVPPSKPECGIEGETIIGNNIQLTC
MDDNGTYECSVSLMSDQDVNAKSRVRLLVLVPPSKPDCSIQGEMVIGNNIQLTC QSKEGSPTPQYSWKRYNILNQEQPLAQPASGQPVSLKNISTDTSGYYICTSSNE
HSAEGSPSPQYSWKSYNAQNQQRPLTQPVSGEPLLLKNISTETAGYYICTSSND EGTQFCNITVAVRSPSMNVALYVGIAVGVVAALIIIGIIIYCCCCRGKDDNTED
VGIESCNITVAPRPPSMNIALYAGIAGSVFVALIIIGVIVYCCCCREKDDKDQD KEDARPNREAYEEPPEQLRELSREREEEDDYRQEEQRSTGRESPDHLDQ
REDARPNRAAYQVPKKEQKEISRGREDEDDHRHEDRWSSGRSTPDQPFQ
```

FB-5
100-310
A33

1M Hydroxylamine pH 7.5

FB-5
100-310
A33

1M Tris pH 7.5

ISOLATED NUCLEIC ACID WHICH ENCODES PROTEIN WHICH BINDS TO A33 ANTIBODY

CROSS REFERENCE TO RELATED APPLICATIONS

This application is a continuation-in-part or Ser. No. 08/597,495, filed Feb. 2, 1996, now U.S. Pat. No. 5,712,369 which is a continuation-in-part of U.S. patent application Ser. No. 08/511,876 filed on Aug. 4, 1995, now abandoned entitled Colon Cell and Colon Cancer Cell Associated Protein and Peptides, both of which are incorporated herein by reference.

FIELD OF THE INVENTION

This invention is directed to human colon cell and colon cancer cell associated antigens, nucleic acid molecules, proteins and peptides. Specifically, the proteins and peptides of the invention, which are encoded by the nucleic acid molecules of the invention, are found both in and on the surface of human colon cells and human colon cancer cells, and bind to colon cancer antibodies. The protein, in a monomeric form, has a molecular weight of about 40–45 kD as determined by SDS gel electrophoresis under non-reducing conditions and about 49–55 kD when subjected to SDS-PAGE under reducing conditions. This protein, peptide fragments thereof and multimeric thereof can be used to develop reagents and methods useful in the diagnosis and treatment of cancer.

BACKGROUND OF THE INVENTION

Colorectal carcinoma is a malignant neoplastic disease. There is a high incidence of colorectal carcinoma in the Western world, particularly in the United States. Tumors of this type often metastasize through lymphatic and vascular channels. Many patients with colorectal carcinoma eventually die from this disease. In fact, it is estimated that 62,000 persons in the United States and 8000 persons in Australia die of colorectal carcinoma annually.

To date, systemic therapies and chemotherapies have been developed for the treatment of colorectal cancer. However, no therapies have exhibited sufficient anti-tumor activity to prolong the survival of colorectal carcinoma patients with metastatic disease, with any degree of reliability. As a result, a need still exists to develop methods and products for the successful treatment of colorectal carcinoma.

Monoclonal antibody A33 is a murine immunoglobulin that has undergone extensive preclinical analysis and localization studies in patients (see Welt et al., *J. Clin. Oncol.*, 8:1894–1906 (1990), Welt et al., *J. Clin. Oncol.*, 12:1561–1571 (1994), and Welt et al. *J. Clin. Oncol.* 14: 1787–1797 (1996). This antibody binds to an antigen found in and on the surface of normal colon cells and colon cancer cells. This antigen is known as the A33 antigen.

In carcinomas originating from the colonic mucosa, the A33 antigen is expressed homogeneously in more than 95% of cases. The A33 antigen has not been detected in a wide range of other normal tissues studied. Its restricted expression defines this system as essentially "organ-specific" (colon, rectum and small bowel).

Immunofluorescence experiments have revealed that mAb A33 is internalized into the macropinosomes of A33 antigen-positive cells in vitro (Daghighian et al;. *J. Nuc. Med.*, 37: 1052–1057 (1996). In a mouse model, mAb'A33 has been found to localize to xenografts of human colon cancer in substantial amounts, and it can be identified in the cytoplasm of transplanted colon cancer cells within the first hour after administration. Rapid tumor localization and high level of antibody uptake by tumors are thought to be related to the following factors: (1) A33 antigen is not secreted, and targeting of mAb A33 to tumor cells is therefore not impeded by shed A33 antigen diffusing from tumor cells to the vascular system; (2) mAb A33 is rapidly internalized into the cell once it binds to A33 antigen on the cell membrane, thereby increasing the amount of cell associated antibody; and (3) some colon cancer cell lines express large amounts of A33 antigen, binding up to 800,000 mAb A33 molecules per cell. Due to these properties, a need exists to isolate, characterize and sequence the A33 antigen, as well as related proteins with similar characteristics.

Many purification protocols typically utilize reduction steps in order to analyze proteins of interest by SDS-gel electrophoresis. In this way, proteins can be identified and monitored more easily. The inventors of the instant application found that surprisingly, by utilizing reducing conditions, they were unable to identify the target A33 protein by Western blotting. Standard techniques had to be changed so as to completely remove reducing steps in order to identify, monitor and characterize the A33 antigen of the invention. Once the antigen was isolated, studies on its behavior under reducing conditions could be carried out.

Purification of the A33 antigen has been further complicated by co-migration of other proteins, including actin, to about the same position on one and two dimensional gel electrophoresis. In addition, mAb A33 binds non-specifically to actin. The inventors of the instant application identified the Fc. regipon of the antibody as being responsible for the non-specific binding to actin. Removal of the Fc region has allowed the inventors to prevent actin binding. As actin is not a cell surface antigen on colon carcinoma cells, and is not sensitive to reduction, it became clear to the inventors that actin could not be the target for monoclonal antibody A33.

The difficulty in identifying, isolating and characterizing this antigen is evidenced by the fact that although the existence of the A33 antigen has been known for more than a decade, this is the first successful purification, isolation and sequencing of the antigen.

As described herein, the inventors of the instant application have identified, isolated and characterized the A33 antigen. The inventors have also isolated cDNA encoding the A33 antigen, determined the nucleotide sequence of the cDNA, and deduced the amino acid sequence for the A33 antigen. The A33 antigen, also referred to herein as the A33 protein, can be utilized to develop clinical reagents and methods useful in the prognosis, diagnosis and treatment of cancer and other diseases, in particular, cancers such as colon, rectum, gastric and small bowel mucosa cancer.

SUMMARY OF THE INVENTION

This invention is directed to an isolated protein which is found inside and on the surface of normal human colon cells and human colon cancer cells, as well as to peptide fragments of said protein. The protein and peptides are bound by the A33 colon cancer antibody or by polyclonal antibodies raised against regions of the protein sequence. When analyzed by SDS gel electrophoresis, the isolated glycoprotein of the invention has a molecular weight of about 40–45 kD, when non-reducing conditions are utilized and about 49–55 kilodaltons under reducing conditions. This invention further relates to nucleic acid molecules encoding said protein, and to the use of said glycoprotein, peptides and nucleic acid molecules in the diagnosis and treatment of cancer.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 11 is comprised of FIGS. 11A and 11B.

FIG. 12 represents amino acid sequences of peptide fragments in the A33 antigen;

FIG. 13 is a flow chart which shows a protocol used for affinity purification of A33 antigen;

FIG. 16 is comprised of FIGS. 16A and 16B. FIG. 16A, and its continuation FIG. 16B, represent the 2.6kb cDNA which encodes the A33 antigen;

FIG. 17 is a comparison of deduced amino acid sequences for human and murine A33;

DETAILED DESCRIPTION OF THE INVENTION

EXAMPLE 1

Figure 1A:
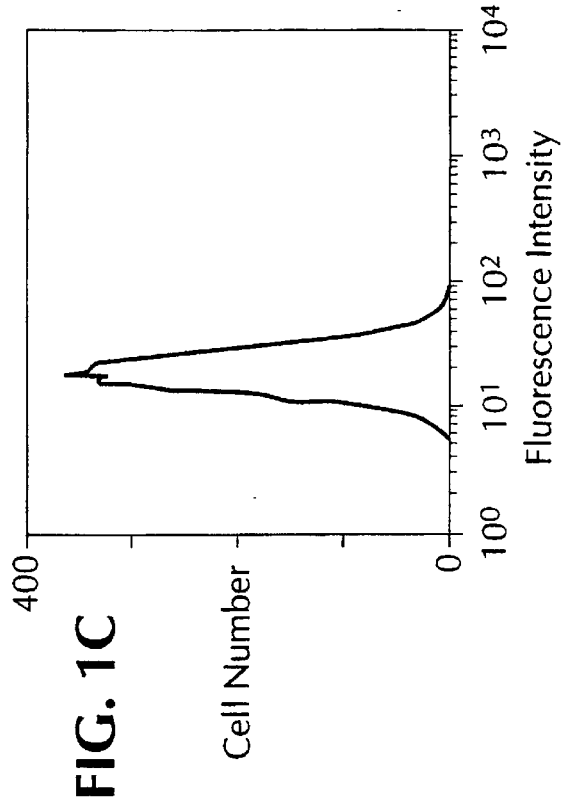
FIG. 1 represents cytofluorographic analysis of the LIM1215 and Hep-2 cells with A33 monoclonal antibody.
Figure 1B:
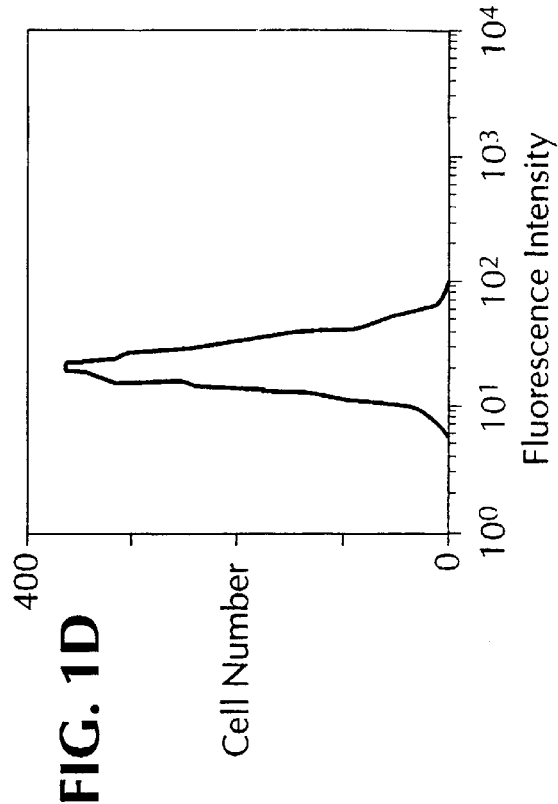
Figure 1C:
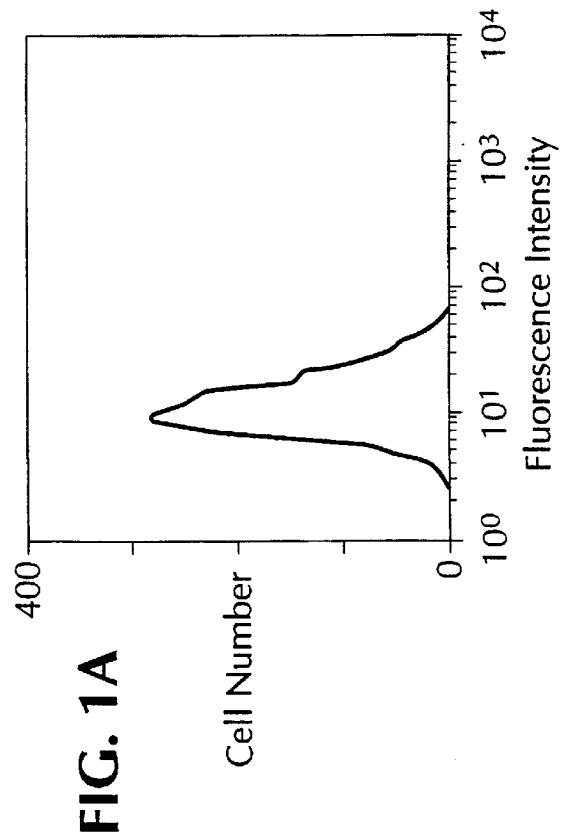
Figure 1D:
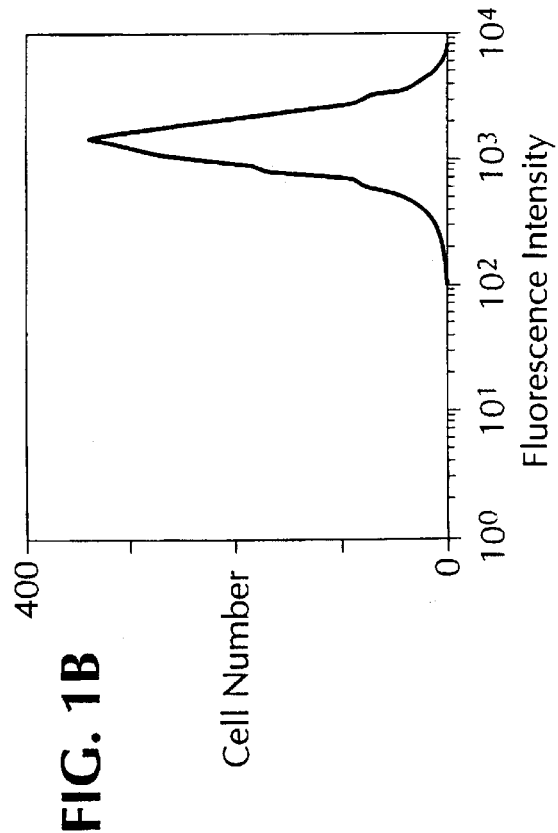

Several colon cancer cultured cell lines, listed in Table 1, were obtained. The LIM1215 cell line was obtained from Ludwig Institute for Cancer Research, Melbourne, Australia. Cell lines SK-CO-17, SK-CO-19, SK-CO-10, SK-CO-11 and SK-CO-15 were obtained from Ludwig Institute for Cancer Research, New York, and Memorial Sloan Kettering Institute, New York. All other cell lines were obtained from the American Type Culture Collection, Rockville, Md.

Using the protocol described by Pfreundschuh et al., *Proc. Natl. Acad. Sci. USA*, 75:5122–5126 (1978), rosetting assays were performed on each of these cell lines using monoclonal antibody A33 (mAb A33), secreted by a hybridoma cell line which was deposited under the Budapest Treaty with the American Type Culture Collection, Rockville, Md. and catalogued as ATCC No. HB 8779. mAb A33 has an isotype of IgG2a and, as described herein, binds to an antigen denoted A33 which is present in and on the surface of human colon carcinomas. Several of the colon carcinoma cell lines were found to be A33-positive, as determined by resetting assays, immunoassays and immunohistochemistry (see Table 1 which follows).

TABLE 1

REACTIVITY OF mAb A33 WITH HUMAN COLON CANCER CELL LINES

| Cell Line | Rosetting A. Titer | Western Blot | Immune precip. |
|---|---|---|---|
| A33 Positive Colon Lines | | | |
| LIM 1215 | $2^{13}$ | +++ | ++ |
| LOVO | $2^{12}$ | + | |
| LS 174T | $2^{12}$ | | |
| LS 180 | $2^{11}$ | ++ | |
| NCI-H508 | $2^{12}$ | +++ | ++ |
| SK-CO-17 | $2^9$ | + | |
| SK-CO-19 | $2^{13}$ | | |
| SNC-2B | $2^{12}$ | | |
| SW403 | $2^{13}$ | + | |
| SW1222 | $2^{12}$ | +++ | ++ |
| COLO 205 | | + | + |
| ASPC-1 (pancreatic) | $2^{13}$ | ++ | ++ |
| A33 Negative Colon Lines | | | |
| DLD1 | — | | |
| HCT15 | — | — | |
| HT29 | — | — | |
| SK-CO-10 | — | — | |
| SK-CO-11 | — | | |
| SK-CO-15 | — | | |
| SW480 | — | | |
| SW620 | — | — | — |
| SW837 | — | | |
| SW1116 | — | — | |
| SW1417 | — | | |

EXAMPLE 2

The LIM1215 colonic cell line, which was positive in the resetting assays of Example 1, was grown in RPMI medium containing 10% fetal calf serum. Confluent cells ($10^6/cm^2$) were passaged using Trypsin-Versene solution. Cells were seeded 1/10 into tissue culture dishes containing 25 ml RPMI 1640 supplemented with 10% fetal calf serum, 1 µg/ml hydrocortisone, 0.025 U/ml insulin and 10.82 µg/ml α-thioglycerol. The dishes were incubated at 37° C. in an atmosphere of 5% $CO_2$ for 5 days. After removing the media, cells were washed with PBS before being removed from the surface using a cell scraper. Cells were washed in PBS and resuspended at $10^9$ cells/ml.

A33 antigen expression on the surface of the LIM1215 colonic carcinoma cell line was then analyzed by flow cytometry following standard techniques. The Hep-2 epidermoid carcinoma cell line (Boring et al., *Cancer J. Clin.*, Vol. 44, pp. 7–26 (1994)) was used as a negative control. The cells were washed and resuspended at $5 \times 10^6$ cells/ml in 500 μl of PBS containing 5 mM EDTA and 5% fetal calf serum. The cells were incubated with 5 μg A33 mAb for 30 minutes at 4° C. After washing with buffer, the cell/antibody complexes were incubated with fluorescein-conjugated anti-murine IgG (⅒₀ dilution). A negative control was performed by staining the cells with an isotopically matched non-related antibody (5 μg) followed by fluorescein-conjugated anti-murine IgG alone. Flow cytometry was performed using a FACScan flow cytometer (Becton Dickinson, San Jose, Calif., U.S.A.).

FIG. 1 shows cytofluorographic analysis of LIM1215 and Hep-2 cells with A33 monoclonal antibody. The entire population of LIM1215 cells exhibited a strong homogeneous fluorescence (panel B) when incubated with A33 mAb, compared with the fluorescence obtained with the control antibody (panel A). The profiles shown in the panels obtained with the Hep-2 cells (C and D) were overlapping, indicating no detectable A33 mAb binding to these cells. The X axis shows the fluorescence intensity (log scale) and the Y axis shows the cell number.

EXAMPLE 3

Figure 2:
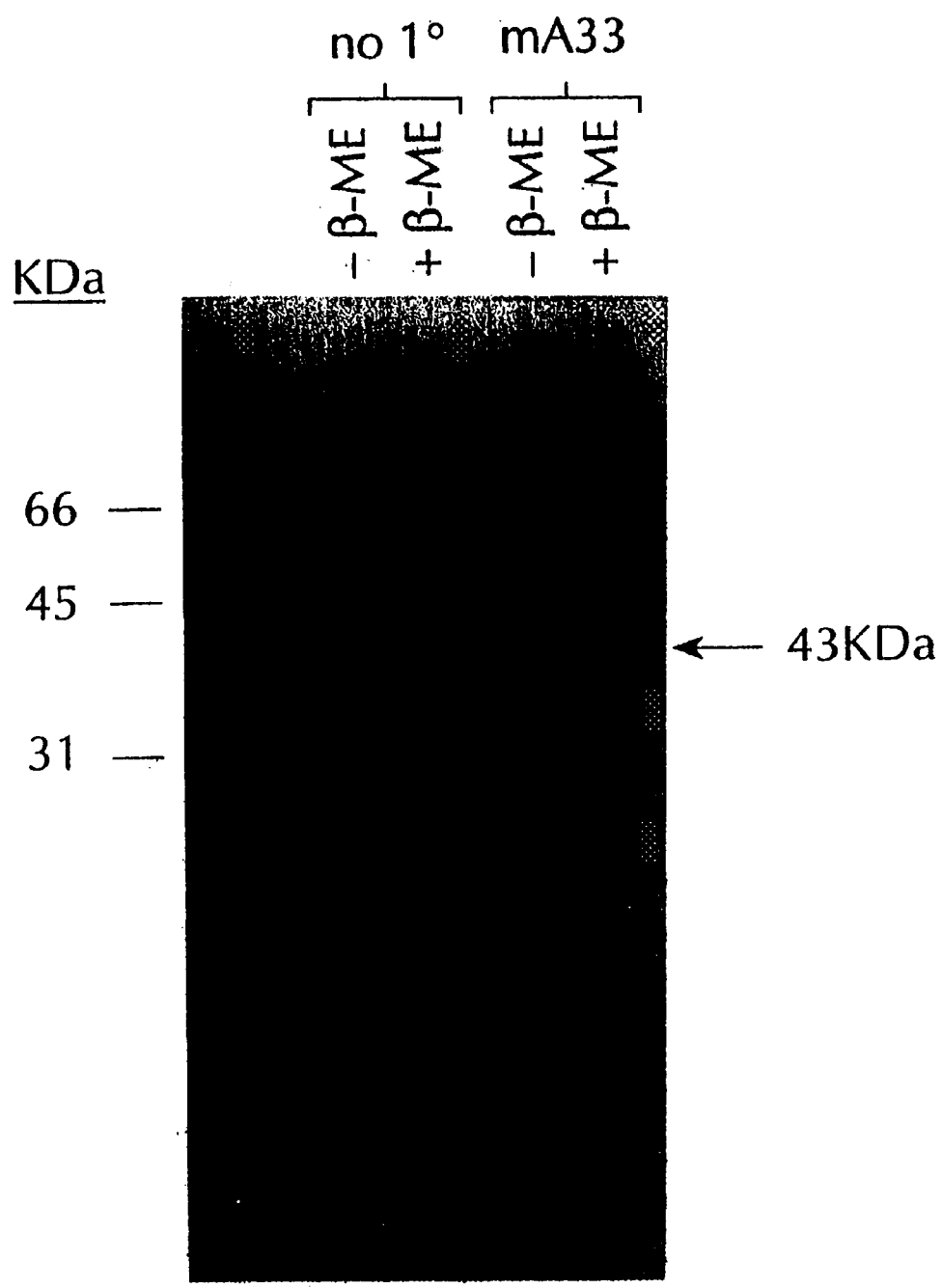
FIG. 2 shows that A33 antigen is detectable by Western blot after SDS gel electrophoresis using non-reducing conditions, but not detectable after SDS gel electrophoresis using reducing conditions. "-B-ME" indicates non-reducing conditions and "+-BME" refers to reducing conditions.

Cell lines which were A33-positive in resetting assays (Table 1) were lysed using 0.3% Triton X-100 in PBS, pH 7.4. Other detergents known to those skilled in the art can also be used to lyse A33-positive cells. The cell lysates of nine A33-positive cell lines and, in addition, five A33-negative cell lines (controls) were probed for A33 antigen expression by Western blot analysis using non-reducing conditions. A molecule with a molecular weight of about 43 kD was detected by Western blotting with mAb A33 in lysates from colon cancer cells which were A33-positive by resetting assay. This molecule was not detected in lysates obtained from cell lines which tested negative for A33 in resetting assays, or by antibodies other than mAb A33, including anti-actin mAb. The A33 antigen was detectable by Western blot analysis only after SDS gel electrophoresis using non-reducing conditions. The A33 antigen was not detectable using reducing conditions. The Western blot shows in FIG. 2 utilized A33 antigen obtained by affinity purification from SW1222 cells. The upper band (FIG. 2) indicates multimeric form of the A33 protein.

EXAMPLE 4

A33 antigen was immunoprecipitated from colon carcinoma cell lysates. In order to do this, colon cancer cells were labeled with $^3$H-GlcNAc or $^{35}$S using standard techniques known to those skilled in the art. Cell lysates which were A33 positive by rosetting assays, and which exhibited a band of about 43 kD by SDS gel electrophoresis under non-reducing conditions, were immunoprecipitated with monoclonal antibody A33.

Figure 3A:
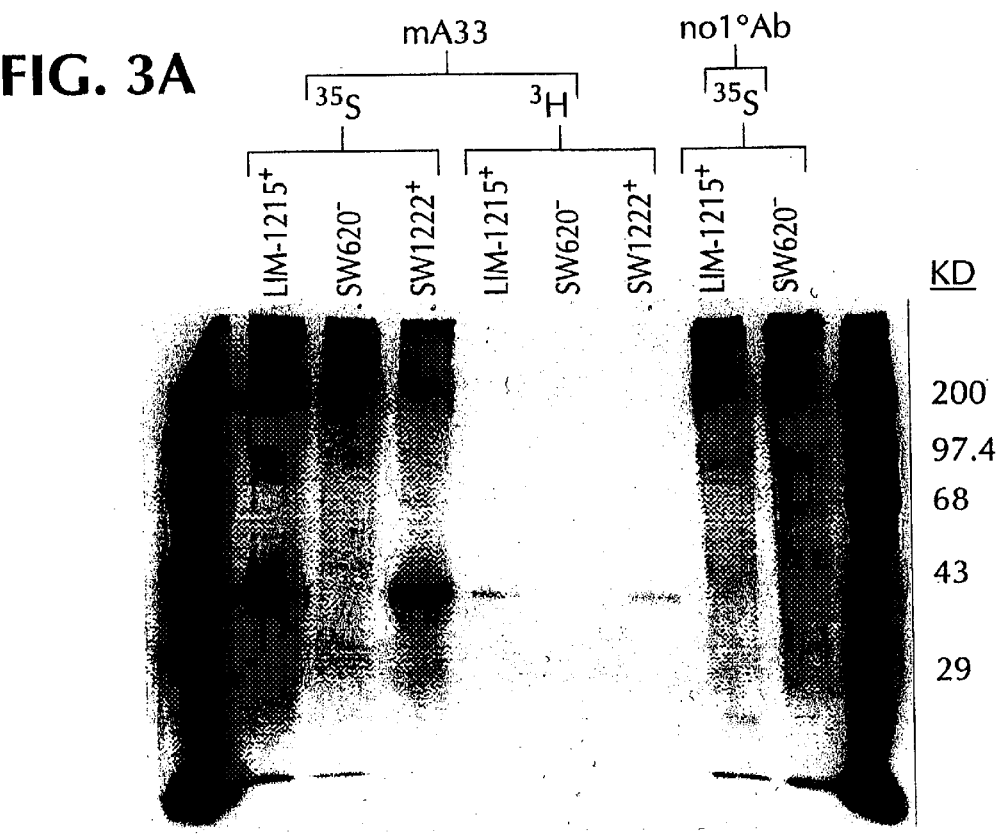
FIG. 3 shows immunoprecipitation of cell lysates with or without mAb A33.
Figure 3B:
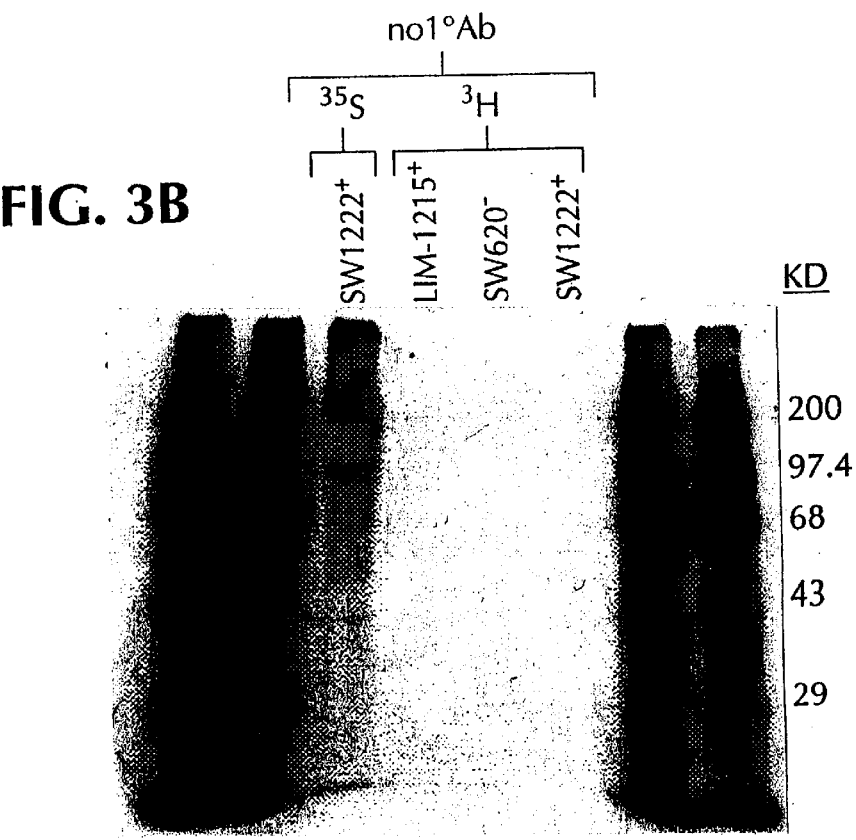

FIG. 3 shows that a molecule was immunoprecipitated from A33-positive lysates which has a molecular weight of about 43 kD. This band was not precipitated by lysates which were A33-negative in rosetting assays. In addition, this band was not precipitated by antibodies other than mAb A33 ("no. 1°Ab" indicates that mAb A33 was not used). Since $^3$H-GlcNAc is a carbohydrate, which is incorporated into the glycosylation side of glycoproteins, these results suggest that the A33 antigen contained in the band is a glycoprotein. Additional evidence in support of this is provided in examples which follow.

EXAMPLE 5

Figure 4A:
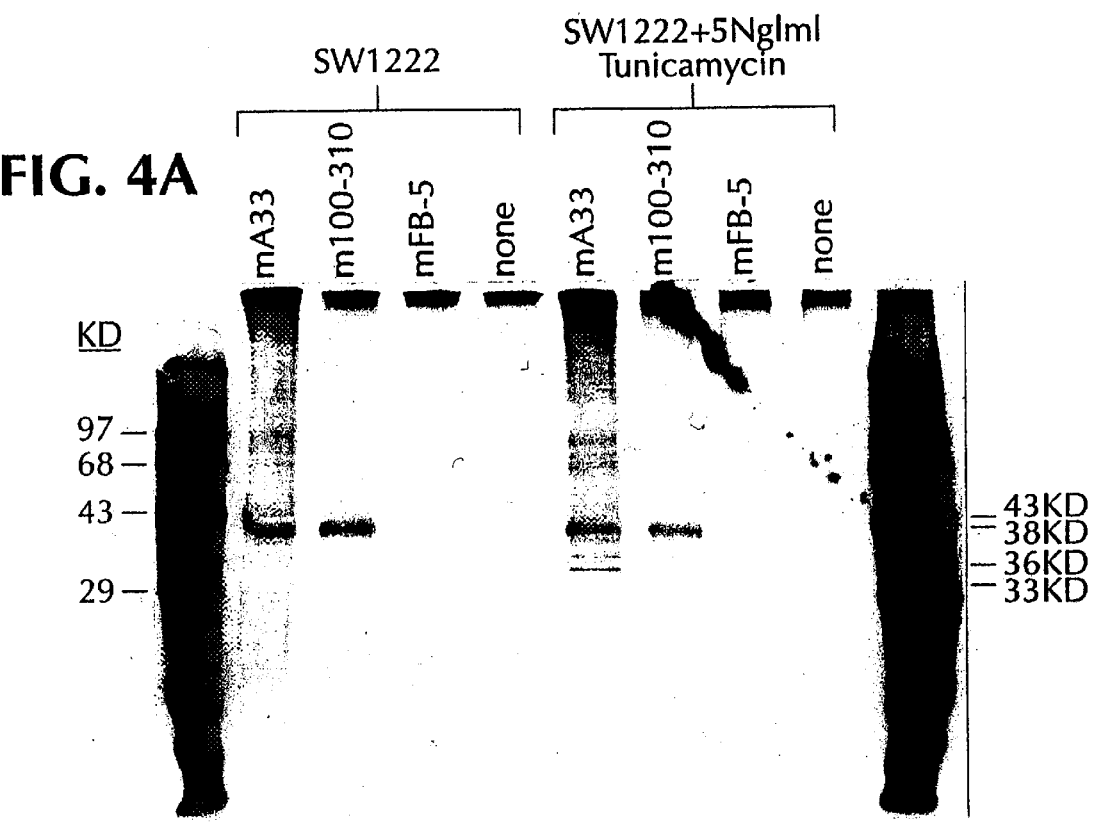
FIG. 4 shows immunoprecipitation of cell lysates which were or were not incubated with tunicamycin.
Figure 4B:
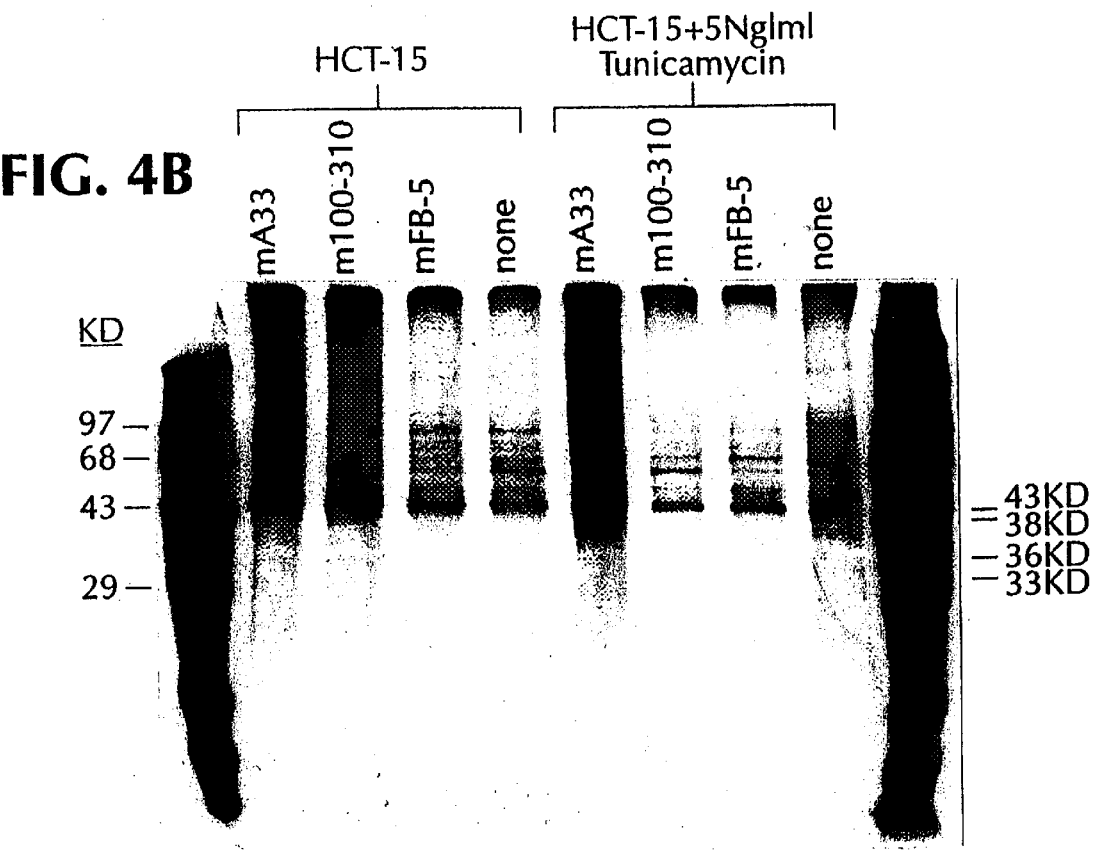

$^{35}$S-labeled SW1222 cells were incubated with 5 μg/ml tunicamycin for 18 hours. Tunicamycin is known to block N-glycosylation of glycoproteins. These cells, as well as cells which were not incubated with tunicamycin, were lysed and subjected to immunoprecipitation with A33 antibody, FB-5 antibody (control) or no antibody (control). FIG. 4 shows the immunoprecipitation results.

Of the cells which were not incubated with tunicamycin, immunoprecipitation with A33 antibody showed a band at about 43 kD. Immunoprecipitation with antibody FB-5, which was an isotype control or no antibody, showed no such 43kD band. Of the cells incubated with tunicamycin, immunoprecipitation with A33 antibody showed a band at 43kD, as well as three other bands of lower molecular weight. These lower molecular weight bands indicate the presence of A33 antigen wish a different degree of glycosylation due to the presence of tunicamycin. This provides further evidence that the A33 antigen is a glycoprotein, and contains N-linked oligosaccharides.

EXAMPLE 6

A33 antigen was identified using 2-dimensional gel electrophoresis under non-reducing conditions. First, the LIM1215 colonic cell line was grown in RPMI medium containing 10% fetal calf serum. Confluent cells ($10^6/cm^2$) were detached from the plastic dish using Trypsin-Versene solution. Cells were seeded ⅒ into tissue culture dishes (150×20 mm) containing 25 ml RPMI 1640 supplemented with 10% fetal calf serum, 1 μg/ml hydrocortisone, 0.024 U/ml insulin and 10.82 μg/ml α-thioglycerol, as described above. Dishes were incubated at 37° C. in an atmosphere of 5% $CO_2$ for 5 days. After removing the media, cells were washed with PBS before being removed from the surface using a cell scraper. Cells were washed in PBS and resuspended at $10^9$ cells/ml.

Next, A33 antigen was extracted from $3 \times 10^8$ LIM1215 cells using 0.3% Triton X-100 in 10 mM Tris-HCl buffer (pH 7.4).. The extract was diluted 1:1 with sample buffer comprised of arginine/lysine buffer, pH 10, containing 30k glycerol, and electrophoresed on small (8×8 cm) Novex 2-dimensional gel electrophoresis gels under non-reducing conditions.

Figure 5A:
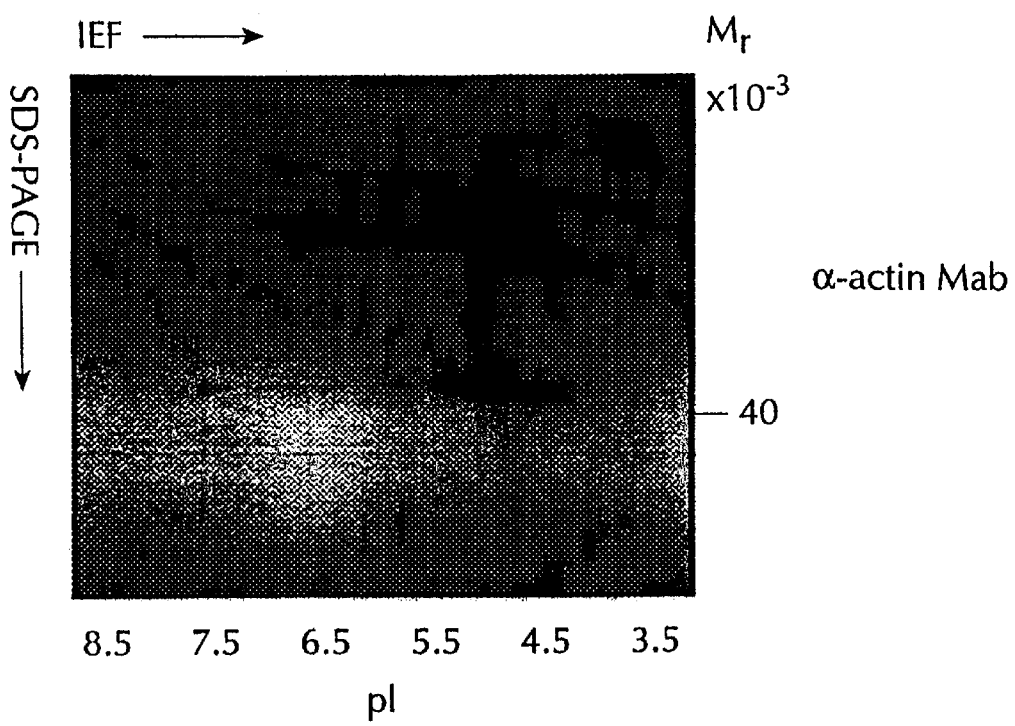
FIG. 5 is comprised of FIGS. 5A and 5B, and represents Western blot analysis of A33 antigen extracted from LIM1215 cells under non-reducing conditions.
Figure 5B:
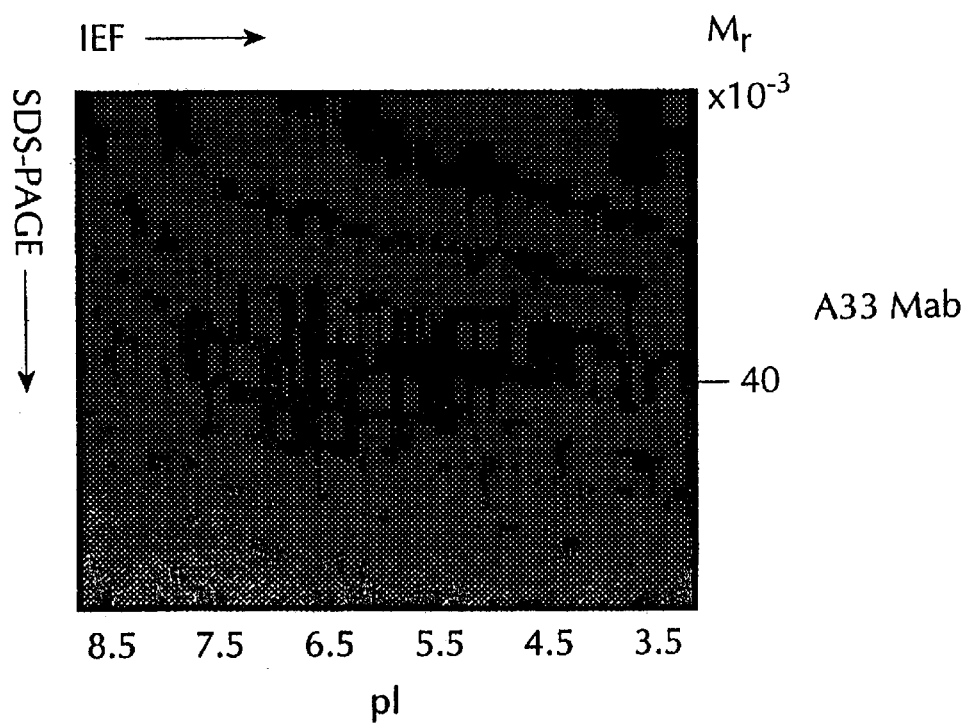

The proteins were separated in the first dimension by isoelectric focusing at a pH of 3.5–8.5, and in the second dimension by SDS-PAGE (10% acrylamide gels). The A33 antigen was localized in the gel by staining with Coomassie Blue R-250, along with immunoblot analysis using mAb A33 (FIG. 5B). For comparison, the staining pattern observed using an anti-actin mAb (FIG. 5A) is shown. Actin is used for comparison because it has similar migration characteristic to the A33 antigen.

EXAMPLE 7

Biosensor analysis was performed on the LIM1215 cell extracts and chromatographic fractions. The extracts and fractions were monitored using ah' instrumental optical biosensor (BIAcore™, Pharmacia Biosensor, Uppsala, Sweden), with a F(ab)'$_2$ fragment of A33 humanized monoclonal antibody immobilized onto the biosensor surface.

To prepare the F(ab)'$_2$ fragment, A33 antibodies were purified (King et al.; *Br. J. Cancer*, Vol. 72, pp. 1364–1372 (1995)). F(ab)'$_2$ fragments were generated by pepsin (1% w/w) digestion of 10 mg A33 mAb in 0.1 M sodium acetate (pH 3.5). These were then purified by size exclusion chromatography on a Sephacryl S-200 (2.8×60 cm) column (Pharmacia Biotech) equilibrated with 50 mM sodium phosphate (pH 7.4) containing 0.15 mM NaCl. The elution was performed at a flow rate of 0.5 ml/min.

The detection of the antigen binding to the F(ab)'$_2$ fragment is based on the phenomenon of surface plasmon resonance, a technique which measures small changes in refractive index at, or near to, the gold sensor surface. Prior to the biosensor assay, cell extracts and chromatographic fractions were diluted to 100 μl, final volume in BIAcore™ buffer (HBS): 10 mM Hepes (pH 7.4) containing 3.4 mM EDTA, 0.15 mM NaCl and 0.005% Tween 20. Samples (30 μl) were injected over the sensor surface at a flow rate of 5 μl/min. Following completion of the injection phase, dissociation was monitored in BIAcore™ buffer at the same flow rate for 360 seconds. Residual bound antigen was eluted and the surface regenerated between injections using 40 μl of 10 mM NaOH. This treatment did not denature the protein immobilized onto the sensor surface as shown by equivalent signals on reinjection of a sample containing the A33 antigen.

Figure 6:
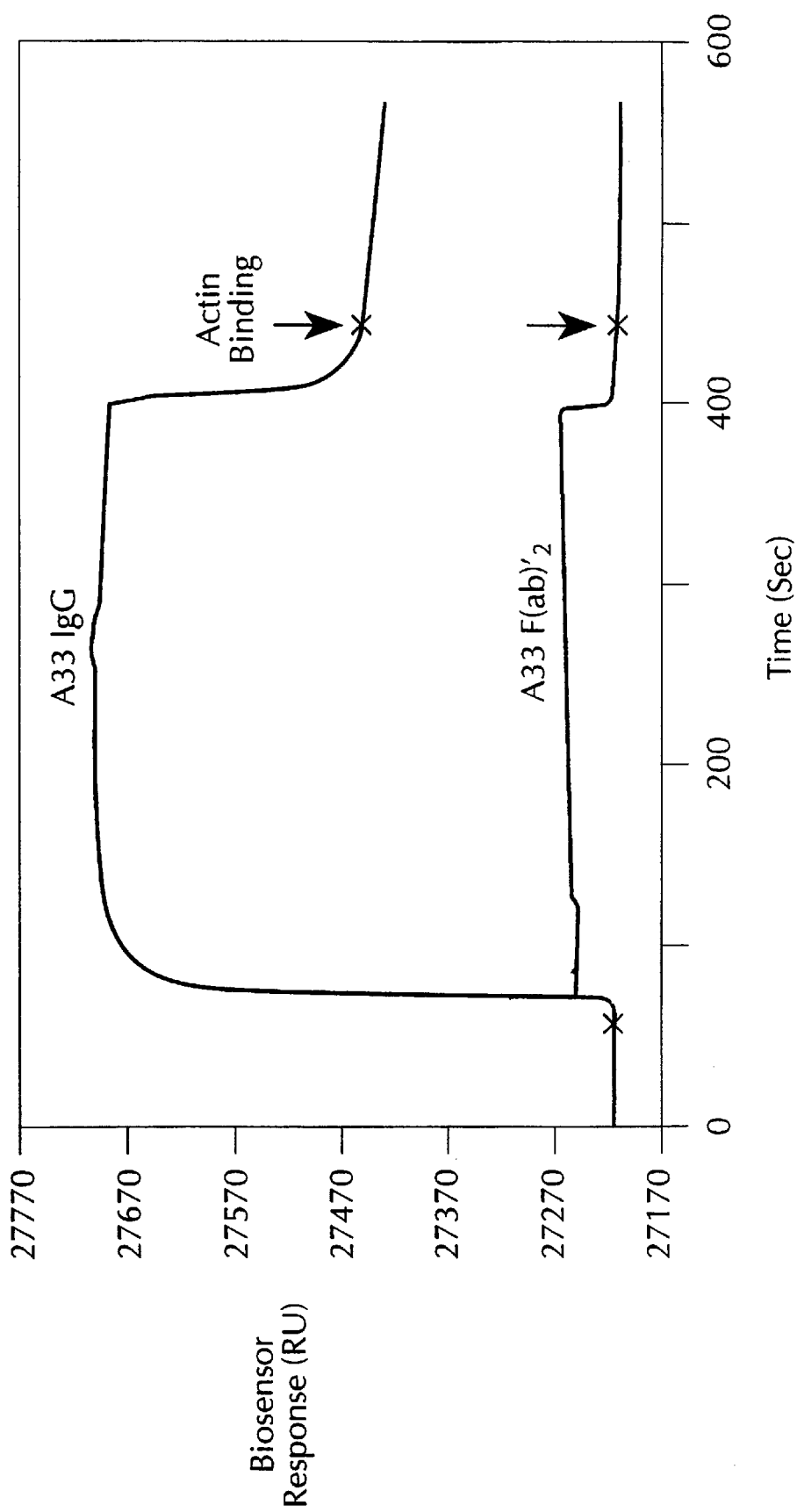
FIG. 6 shows biosensor analysis of the interaction between actin and either A33 IgG or the A33 F(ab)'$_2$ fragment.

FIG. 6 shows biosensor, analysis of the. interaction between actin and either the complete A33 antibody or the A33 F(ab)'$_2$ fragment. A preparation of rabbit, muscle actin (0.3 μg) was injected at a flow rate of 5 μl/min over a sensor surface which had been immobilized/with either whole A33 (upper trace) or A33 F(ab)'$_2$ fragment (lower trace). Protein/protein interactions were-monitored by surface plasmon resonance. At the end of the injection pulse, a signal of 247 RU was observed due to actin binding to A33 IgG, while the signal corresponding to actin binding to A33 F(ab)'$_2$ was only 4 RU (as indicated by arrows).

EXAMPLE 8

Figure 7:
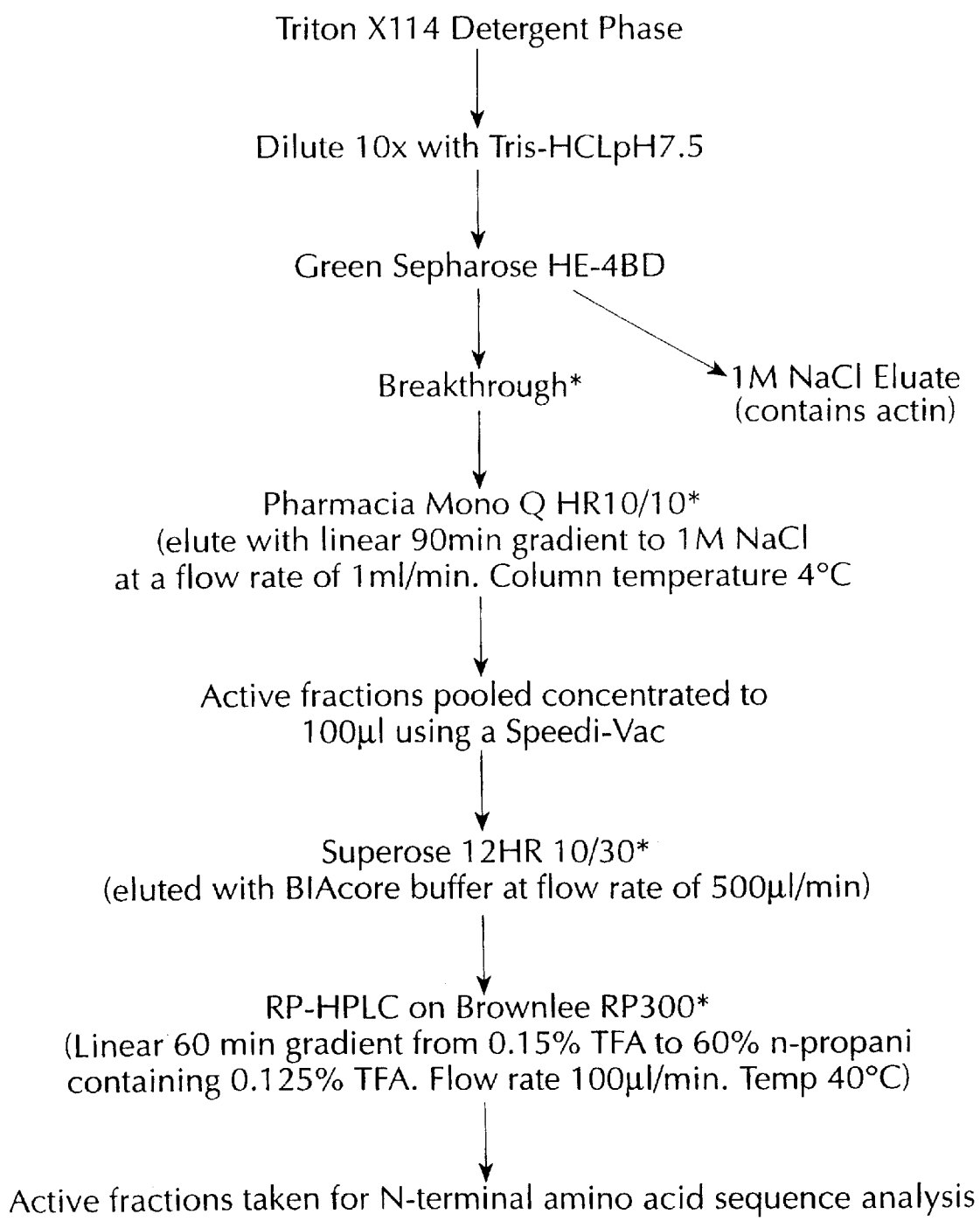
FIG. 7 is a flow chart depicting the chromatographic purification protocol used to purify A33 antigen.

A33 antigen was purified from LIM1215 cells for sequence analysis. FIG. 7 is a flow chart which depicts the chromatographic purification protocol used to purify A33 antigen. To extract A33 antigen, LIM1215 colonic cells (2×10$^9$ cells) were harvested, washed in phosphate-buffered saline (PBS) and solubilized (10$^8$ cells/ml) for 30 minutes at 4° C. with either 0.3% (v/v) Triton X-100 or 1% (v/v) Triton X-114 in 15 mM Tris-HCl (pH 7.4) containing 1 mM PMSF, 1 mM pepstatin, 0.1 mM leupeptin and 0.01 U/ml aprotinin. The resulting extracts were centrifuged twice at 4° C. for 20 minutes at 14,000g. The Triton-X100 supernatant was taken directly for Green-Sepharose HE-4BD chromatography. The Triton X-114 extracted supernatant was layered over 6% sucrose in 15 mM Tris-HCl (pH 7.4) with 0.06k (v/v) Triton X-114, containing the protease inhibitors listed above. The tubes containing the Triton X-114 extracts and the sucrose were incubated at 37° C. for 30 minutes and then centrifuged at 25° C. for 15 minutes at 5,000 g. The detergent phase was collected for chromatographic purification.

In order to perform Green-Sepharose chromatography, Triton-X100 extracts or the Triton X-114 detergent phase were diluted to a final concentration of 0.1% Triton and loaded at 4° C. onto a Green-Sepharose HE-4BD column (100×10 mm ID) connected to a Fast Protein Liquid Chromatography system (FPLC, Pharmacia Biotech, Uppsala,, Sweden). The column was equilibrated with 10 mM Tris-HCl (pH 7.4) containing 0.1t CHAPS (w/v). Bound proteins, including actin, were eluted stepwise with 1M NaCl. The breakthrough contained the A33 antigen, and was collected for anion-exchange HPLC, as described below.

EXAMPLE 9

Western blot analysis was performed throughout purification to confirm the presence of A33 antigen. Electrophoresis and Western blot analysis were performed on precast Phastgels using a Phastsystem separation and control unit (Pharmacia Biotech). Cell extracts and chromatographic fractions were electrophoresed under non-reducing conditions as described by Reid et al, *Electrophoresis, Vol.* 16, pp. 1120–1130 (1995), on 8–25% SDS-PAGE Phastgels or 8–25% native Phastgels and transferred onto PVDF membranes and incubated with A33 monoclonal antibody. RP-HPLC purified A33 antigen was also analyzed by Western blot under non-reducing and reducing conditions using polyclonal anti-N-terminal peptide antibodies (described herein). IgG binding was probed with horseradish peroxidase-labelled goat anti-mouse IgG, goat anti-human IgG or goat anti-rabbit IgG and detected by enhanced chemiluminescence (ECL).

Figure 8A:
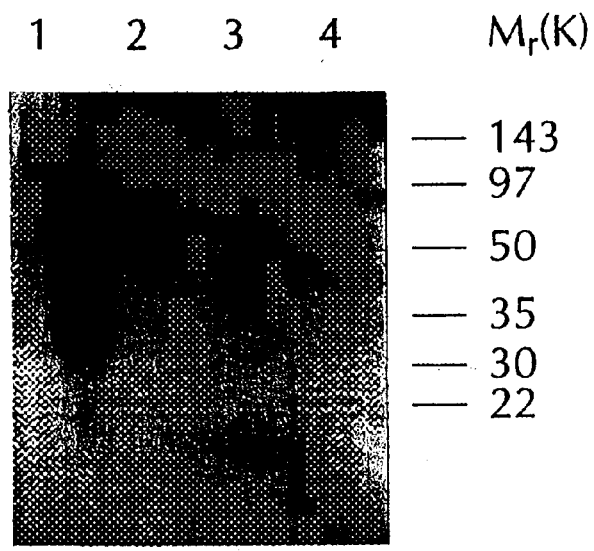
FIG. 8 is comprised of FIGS. 8A and 8B and shows Western blot analysis of Triton X-100 and Triton X-114 extracts of LIM1215-colonic cells, respectively.
Figure 8B:
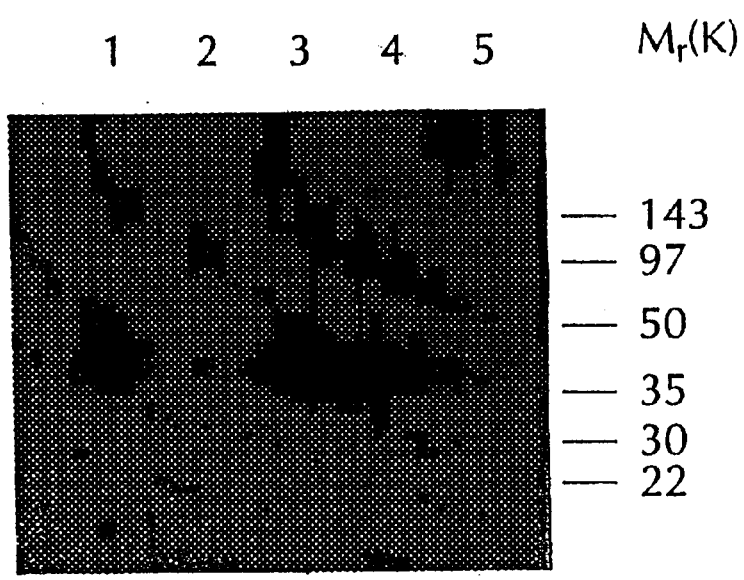

FIG. 8 shows Western blot analysis of the Triton X-100 and Triton X-114 extracts of LIM1215 colonic cells. Panel A shows the following: Lane 1: LIM1215 cells solubilized in 0.3% Triton X-100. Lane 2: Green-Sepharose breakthrough containing the 43K A33 antigen. Lane 3: Green-Sepharose binding proteins eluted with 1M NaCl containing a 41 kD molecular weight band. Lane 4: Rabbit muscle Actin (1 μg).

Panel B shows the following: Lane 1: LIM1215 cells solubilized in 1% Triton X-114. Lane 2: Txiton X-114 aqueous phase. Lane 3: Triton X-114 detergent phase. Lane 4: Green-Sepharose breakthrough. Lane. 5: Green-Sepharose binding proteins eluted with 1M NaCl.

EXAMPLE 10

Following Green-Sepharose chromatography (described above), anion-exchange HPLC was performed. The Green-Sepharose breakthrough was injected at 4° C. onto a Mono Q HR 10/10 column previously equilibrated in 10 mM Tris-HCl (pH 7.4) containing 0.1% (w/v) CHAPS. The proteins were eluted from the column using a linear 0–1M NaCl gradient generated over 90 minutes at a flow rate of 1 ml/min. Fractions (1 ml) were collected automatically using a fraction collector (FRAC 100, Pharmacia Biotech). Proteins were detected by absorbance at 280 nm. The A33 antigen was detected using both Western blotting under non-reducing conditions and biosensor analysis.

Figure 9:
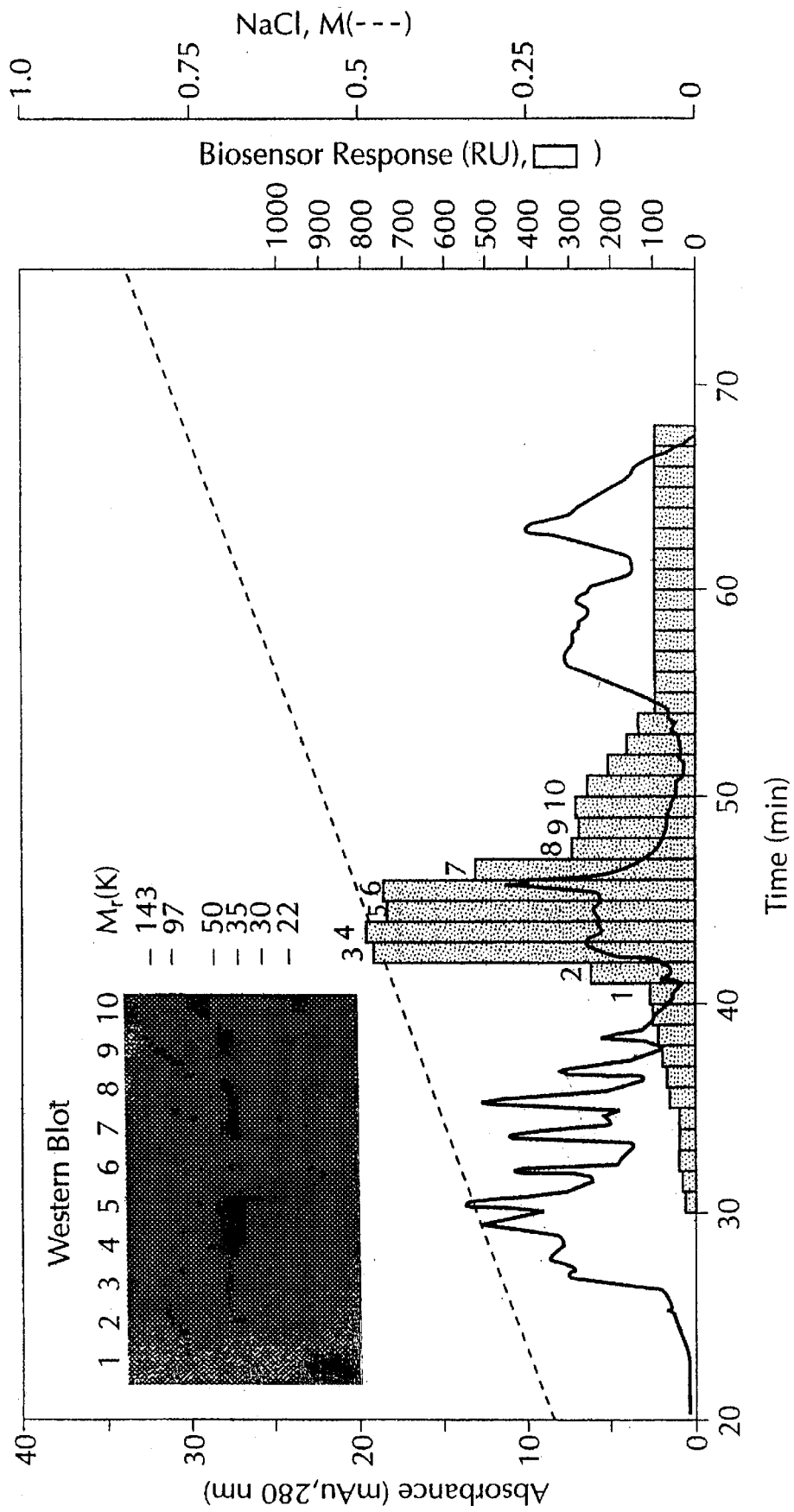
FIG. 9 shows anion-exchange HPLC of the A33 antigen.

FIG. 9 shows anion-exchange HPLC of the A33 antigen. The proteins contained in the Green-Sepharose breakthrough fraction which were loaded onto the Mono Q HR 10/10 anion-exchange column and eluted at a flow rate of 1 ml/min with a linear gradient from 0–1 M NaCl are indicated (—). One ml fractions were collected and aliquots (20 μl) of each of the fractions were taken for biosensor assay. The approximately 43 kD antigen was detected in the labelled fractions by Western blot analysis under non-reducing conditions (inset, FIG. 9) as described herein.

EXAMPLE 11

Next, size-exclusion HPLC was performed. The active fractions eluted from the Mono Q column (10 ml) were concentrated 10 fold using a Speed Vac concentrator (Savant Instruments Inc., N.Y., U.S.A.), dialyzed against PBS containing 0.05% CHAPS (w/v) and loaded at 4° C. onto a Superose 12 HR 10/30 column. Proteins were eluted with PBS containing 0.05% (w/v) CHAPS at a flow rate of 500 μl/min. Fractions (0.5 ml) were collected. Proteins were detected at 280 nm and the A33 antigen was monitored using both Western blotting and biosensor analysis as described above.

Figure 10:
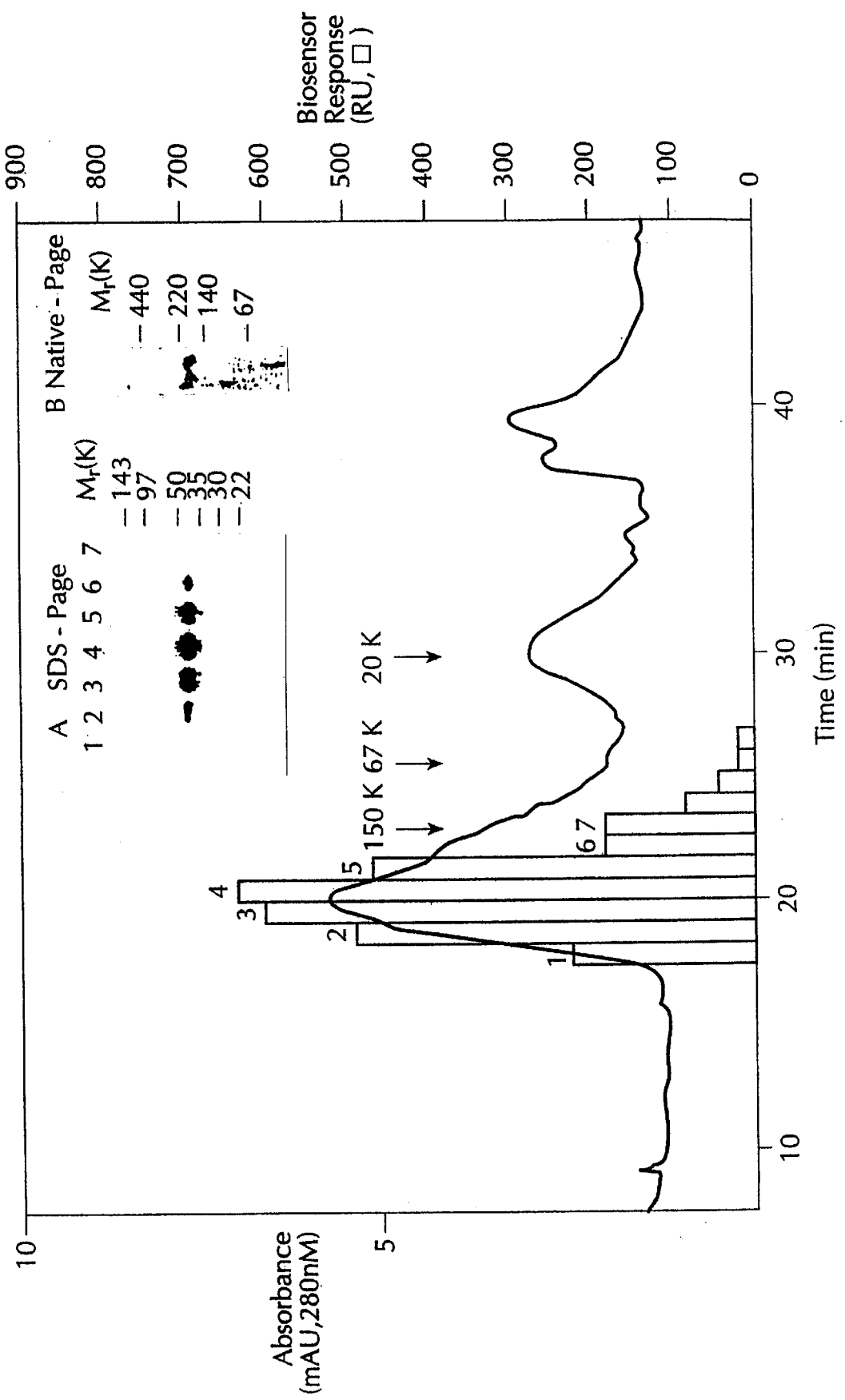
FIG. 10 shows size-exclusion HPLC of the A33 antigen.

FIG. 10 shows size-exclusion HPbC of the A33 antigen. The elution positions of protein calibration standards (BSA dimer, BSA and trypsin inhibitor) are indicated above the chromatographic trace. The A33 antigen was also detected by Western blot analysis under non-reducing conditions (inset A) in the fractions indicated. Immunoblot analysis of a pool of the Superose 12 activity (fractions 2–5) using an 8–25% native gel revealed that the A33 antigen migrated under native conditions (no SDS) with a relative molecular mass of 180 kD (inset B, FIG. 10).

EXAMPLE 12

Reversed-phase HPLC chromatography was then performed. Superose 12 active fractions (2.5 ml) were loaded at a flow rate of 1 ml/min, by multiple 1 ml injections, onto a Brownlee Aquapore RP 300 micropreparative RP-HPLC column (30×2.1 mm ID) equilibrated with the primary solvent, 0.15% (v/v) trifluoroacetic acid (TFA) in water. The proteins were eluted with a linear 60 minute gradient to 60% aqueous n-propanol/0.125% (v/v) TFA at a flow rate of 100 µl/min. The column temperature was 45° C. Protein detection was performed at 215 nm. The A33 antigen was detected: using both Western blotting and biosensor analysis. The peak containing the A33 antigen was repurified and further concentrated using a Brownlee Aquapore RP 300 micropreparative RP-HPLC column (100×1 mm ID) prior to N-terminal sequence analysis, using the gradient conditions described above at a flow rate of 50 µl/min. Eluent fractions were recovered manually.

Figure 11A:
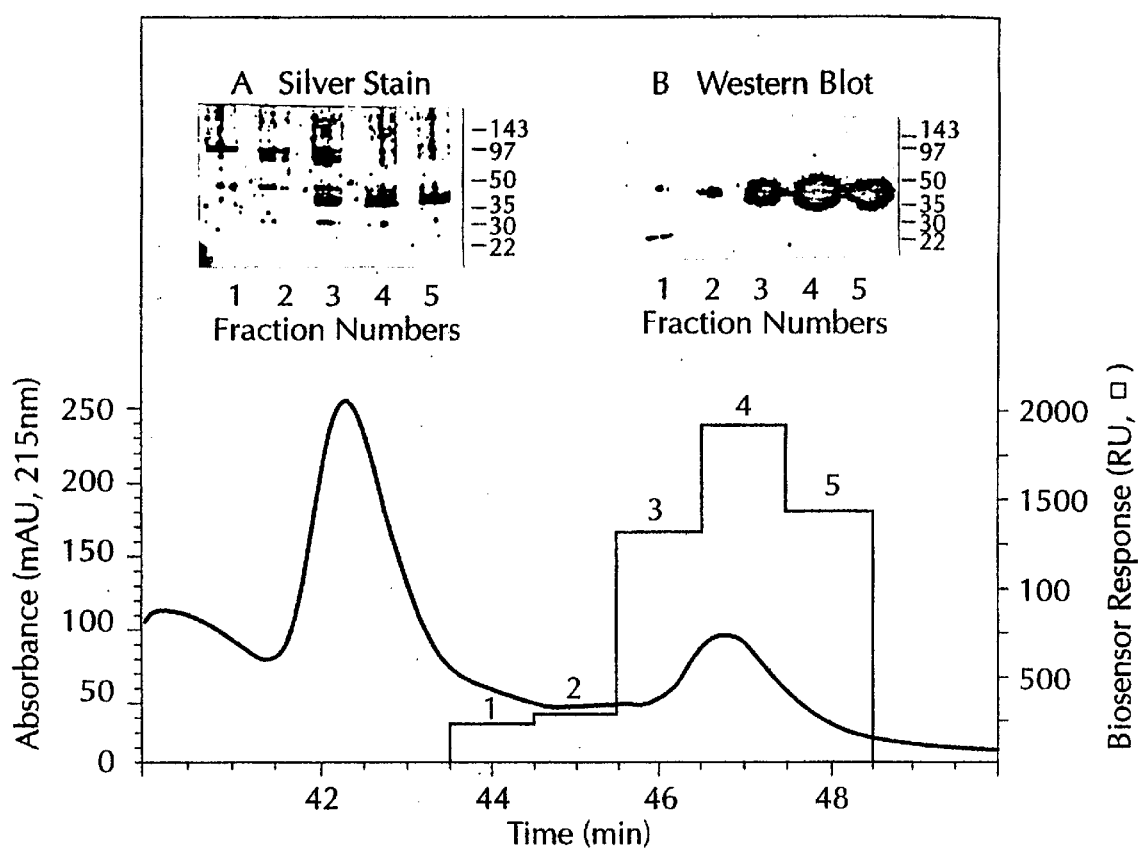
FIG. 11A shows micropreparative RP-HPLC purification of Superose 12 active fractions.
Figure 11B:
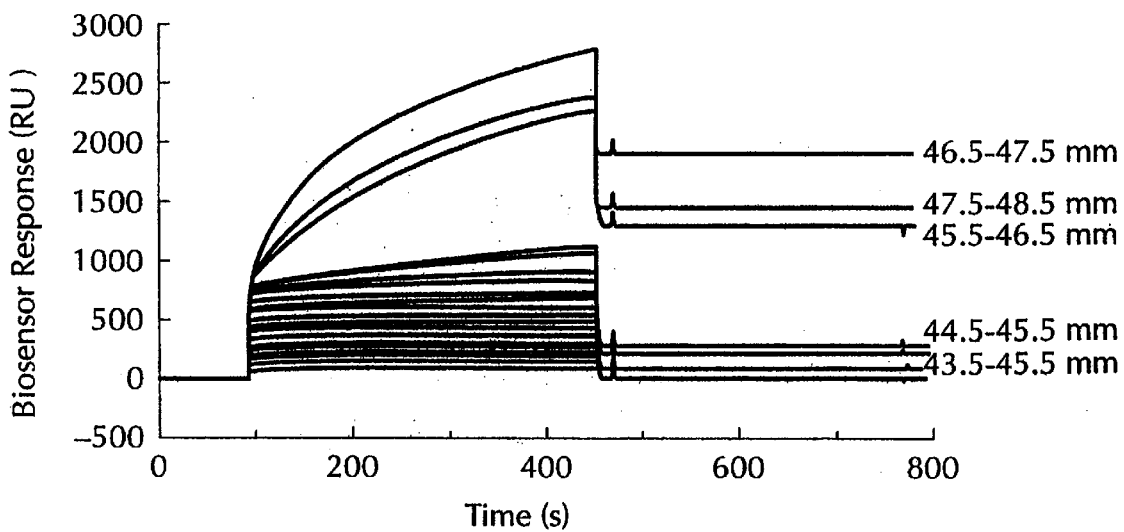
FIG. 11B shows biosensor analysis of the A33 antigen activity in the HPLC fraction.

FIG. 11 shows micropreparative RP-HPLC purification of Superose 12 active fractions. Panel A, main frame, shows the elution profile of the fractions from micropreparative RP-HPLC as analyzed by absorbance at 215 nm and by biosensor. Panel A, inset A, shows aliquots (2 µl) of each fraction, analyzed by SDS-PAGE (8–25% gel, silver stained), and Panel A, inset B, shows a Western blot under non-reducing conditions. Panel B shows biosensor analysis of individual fractions from micropreparative RP-PHLC. Aliquots (20 µl) of each fraction were concentrated using a Speed Vac concentrator and redissolved in 100 µl of RIA-core™ buffer. 30 µl aliquots were analyzed using the biosensor. Activity was found in the fractions eluting between 46 and 48 minutes.

EXAMPLE 13

As discussed above, the A33 antigen-containing reversed-phase HPLC fractions were pooled for amino acid sequence analysis. N-terminal amino acid sequence analysis of purified A33 antigen/protein was performed on a Hewlett-Packard model G1005A protein sensor operated with the routine 3.0 sequencer program described by Reid et al., *Electrophoresis*, Vol. 16, pp. 1120–1130 (1995). The following N-terminus sequence of 30 amino acids was obtained: (SEQ ID NO: 1)

XSVETPQDVLRASQGKSVTLPX-
TYHTSXXXREGLIQWD.

A search of all of the available protein, DNA and expressed sequence tag databases did not reveal any significant amino acid sequence identity of the A33 N-terminus with known proteins.

In addition, A33 antigen-containing reversed phase HPLC fractions were subjected to tryptic digestion as described by Simpson et al., *Eur. J. Biochem.*, Vol. 183, pp. 715–722 (1989). Peptide fragments T1 and T2 were obtained. The amino acid sequences for these peptide fragments are shown in FIG. 12.

EXAMPLE 14

A33 antigen-containing fractions were obtained from SW1222 cells utilizing the protocol shown in FIG. 13. To perform affinity chromatography, the A33 affinity column was prepared according to the protocol described by Schneider et al., *J. Biol. Chem.* Vol. 257, pp.. 10766–10769 (1982). A33 monoclonal antibody was diluted to 1 mg/ml in 0.1 M borate, pH 8.2, and incubated overnight at 4° C. with 1.5 ml Protein A-Sepharose. After washing with 0.1 M borate, pH 9.2, the Protein-A-monoclonal/antibody complex was incubated for 1 hour at room temperature with 20 mM dimethylpimelimidate in 0.1 M borate, pH 9.2. Non-covalently bound antibody was removed with 50 mM glycine, pH 2.5. The remaining active dimethylpimelimidate groups were deactivated by washing and incubating the beads with 0.1 M ethanolamine pH 8.0.

The reversed-phase HPLC fractions were pooled for amino acid sequence analysis sequence analysis was performed as described in Example 13. The following A33 N-terminus sequence was obtained: (SEQ ID NO: 4)

ISVETPQDVLRASQGKSVTLPX-
TYHTSTSSREGLIQWDKL

A sequence search did not reveal any significant amino acid sequence identity with known proteins. This N-terminus sequence was utilized to obtain the cDNA sequence which encodes A33 antigen (described below).

In addition, A33 antigen-containing reversed phase HPLC fractions were subjected to Asp-N endoproteinase digestion as described by Simpson et al., *Eur. J. Biochem.*, Vol. 183, pp. 715–722 (1989). Peptide fragments D1, D2, D3 and D4 were obtained. These peptides were purified by micropreparative RP-HPLC. The amino acid sequences for these peptide fragments are shown in FIG. 12. It was determined that there was a lack of an amino acid in cycle 3 of the Edman degradation of peptide D4. Asp 112 was flanked by Thr at position 114. As this is a classical N-glycosylation motif, evidence was provided that A33 protein is N-glycosylated.

Fractions were also subjected to pepsin digestion, as described by Sarkar et al, *Proc. Nat'l Acad. Sci. U.S.A.*, Vol. 88, pp. 234–238 (1991). Peptide fragment P1 was obtained. The amino acid sequence for peptide fragment P1 is shown in FIG. 12.

RP-HPLC fragments were subjected to Thermolysin/pepsin/Asp-N digestion. Thermolysin digestion was performed as described by Sarkar, supra. Peptide fragments Pc1 and Pc2 were obtained. The amino acid sequences for peptide fragments Pc1 and Pc2 are shown in FIG. 12.

EXAMPLE 15

Immunization studies were performed utilizing an immunogen derived from the amino acid sequence of the N-terminus of A33 antigen. A chemically synthesized peptide, SVETPQDVLRASQGKSVTLP (amino acids 2–21 of SEQ ID NO: 1) was conjugated to KLH and injected,, with adjuvant, into two mice and into two-rabbits. Rabbits were immunized four times at three week intervals. In the first immunization, complete Freund's adjuvant (CFA) was used. In subsequent rabbit immunizations, incomplete Freund's adjuvant (IFA) was used. Mice were immunized four times at two week intervals, using standard adjuvant. Sera were obtained from the rabbits and from the mice. The sera were subjected to Western blot analysis.

Figure 14:
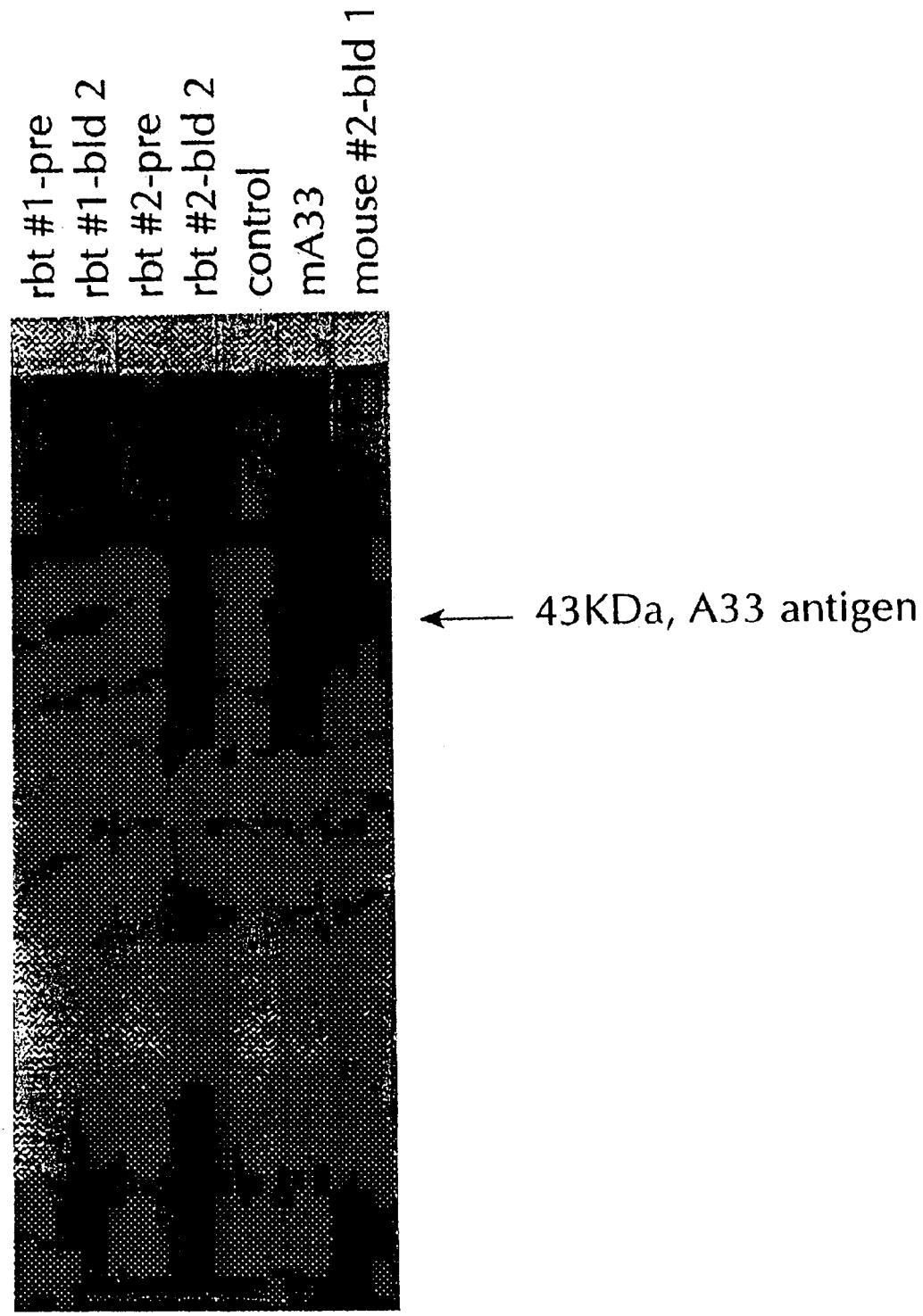
FIG. 14 represents Western blot analysis of sera obtained from mice, and rabbits immunized with chemically synthesized peptide SVETPQDVLRASQGKSVTLP (amino acids 2–21 of SEQ ID NO: 1) conjugated to keyhole limpet hemocyanin (KLH)
Figure 15:
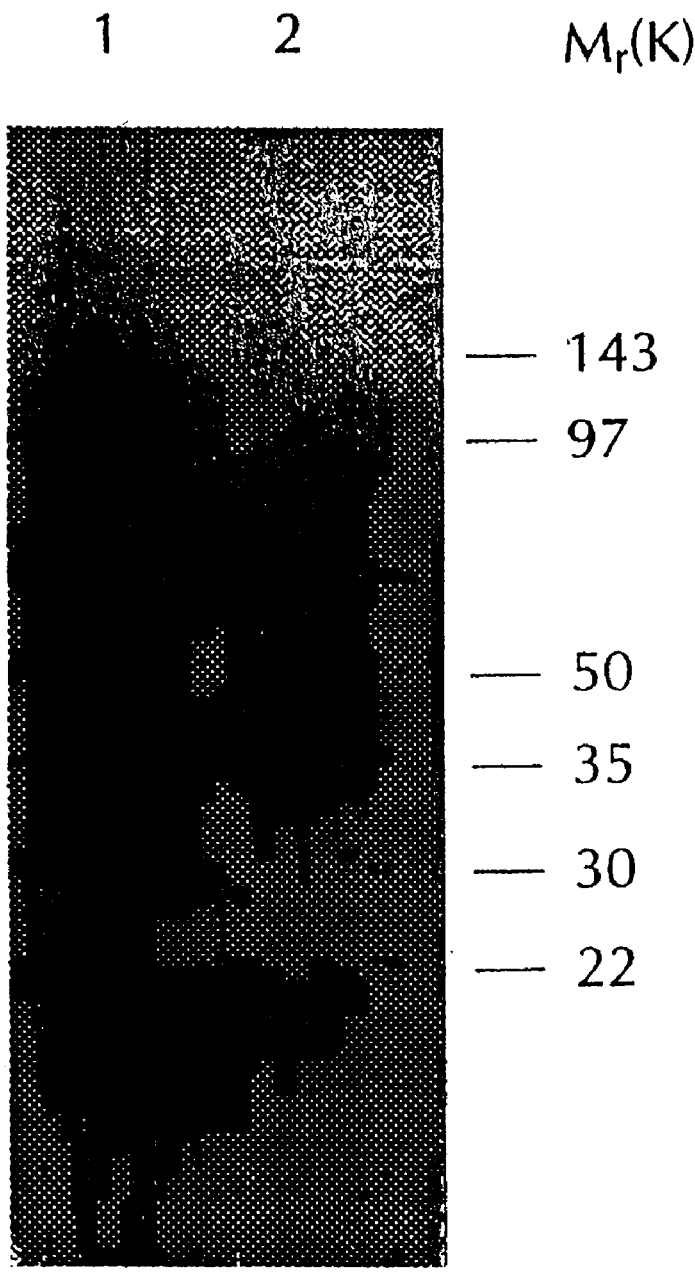
FIG. 15 represents Western blot analysis of the A33 antigen under non-reduced (panel 1) and reduced (panel 2) conditions using an anti-peptide IgG raised against the N-terminus of the A33 antigen.

It was found that both the rabbits and mice developed IgG antibodies which reacted with the peptide, and also with the 43 kD band (the same 43 kD band was recognized by mAb A33) in using cell line SW1222 (FIG. 14). IgG was purified from rabbit immune sera by Protein-A affinity chromatography. Purified IgG was characterized by SDS-PAGE and Western blot analysis for reactivity with LIM1215 cell lysates and purified A33 antigen. The IgG was found to react strongly with the 20 amino acid peptide discussed supra, and with the approximately 43 kD protein which was recognized by mAb A33 under non-reducing conditions. In addition, rabbit IgG anti-serum reacted strongly with whole A33 antigen in reduced form (FIG. 15). HPLC purified A33 antigen from LIM1215 (0.1 µg) was electrophoresed on an 8–25% SDS-PAGE Phastgel under non-reducing (FIG. 15, lane 1) and reducing (FIG. 15, lane 2) conditions and analyzed by Western blot using an anti-peptide IgG raised against residues 2–21 of SEQ ID NO: 1, as described-above. The A33 antigen N-terminus sequence, and fragments thereof, can be used to develop A33 antigen-specific antibodies. These antibodies will recognize and bind, to A33 antigen or fragments thereof, in either reduced or non-reduced form.

EXAMPLE 16

The amino acid sequence of the A33 N-terminus of A33 protein was used to clone A33 protein cDNA. Poly (A)⁺RNA (80 µg) was prepared in-house from confluent LIM1215 cells by two rounds of enrichment on columns of oligo (dT) cellulose using standard procedures. A LIM1215 cDNA library was custom-synthesized in the λZAPII expression vector by Clontech (Palo Alto, Calif., U.S.A.) using oligo (dT) and random hexamer primers to prime first strand DNA synthesis (standard procedures), using this mRNA.

Successful screening of the library was achieved with a DNA probe generated from the LIM1215 cDNA library using the polymerase chain reaction (PCR). Six 17mer antisense oligonucleotides (R9–R14), each with only 8-fold degeneracy, were designed to correspond to amino acid residues 34–39 of the A33 antigen N-terminal sequence (L I Q W D K (amino acids 34–39 of SEQ ID NO: 4)) as follows:

```
Primer #1477 (R9) 5' A(R) (Y) TT (R) TCCCACTGAAT (SEQ ID NO: 12)
Primer #1478 (R10)5' A(R) (Y) TT (R) TCCCATTGAAT (SEQ ID NO: 13)
Primer #1479 (R11)5' A(R) (Y) TT (R) TCCCACTGGAT (SEQ ID NO: 14)
Primer #1480 (R12)5' A(R) (Y) TT (R) TCCCATTGGAT (SEQ ID NO: 15)
Primer #5915 (R13)5' A(R) (Y) TT (R) TCCCACTGTAT (SEQ ID NO: 16)
Primer #5916 (R14)5' A(R) (Y) TT (R) TCCCATTGTAT (SEQ ID NO: 17)
```

These were paired with sense primers designed to hybridize to sequences present in the backbone of the λZAPII vector and were used in PCR reactions with the amplified LIM1215 cDNA library as the source of A33 antigen template. The successful reaction occurred with primers described below. For PCR reaction, the template used was amplified LIM1215 cDNA library in λZAPII vector. The primers used were as follows: KS primer 5'CGAGGTC-GACGGTATCG (SEQ ID NO: 18) (17mer) (hybridizes to a sequence in multicloning site of λZAPII vector); and R10 primer (described above).

The reaction conditions were as follows:

| | |
|---|---|
| cDNA library (10" pfu/ml) | 1 µl |
| 10 × T'aq ™ buffer | 5 µl |
| 1.5 mM NTPs | 4 µl |
| 15 mM MgCl₂ | 5 µl |
| KS (50 pmoles/µl) | 1 µl |
| R10 (50 pmoles/µl) | 1 µl |
| Water | 32.5 µl |
| Taq polymerase | 0.5 µl (added last in Hot |
| | 50.0 µl Start) |

The touchdown program used in the PCR was as follows:

| | |
|---|---|
| 1 | 95° C. × 5 min |
| 2 | 95° C. × 1 min |
| 3 | 60° C. × 1 min |
| | −2° C. in subsequent cycles |
| 4 | 72° C. × 2 min |
| 5 | Go to (2) eleven times |
| 6 | 95° C. × 1 min |
| 7 | 37° C. × 2 min |
| 8 | 72° C. × 2 min |
| 9 | 95° C. × 1 min |
| 10 | 45° C. × 2 min |
| 11 | 72° C. × 2 min |
| 12 | Go to (9) thirteen times |
| 13 | 72° C. × 5 min |
| 14 | 4° C. hold |

Three products were generated, and were 1.4 kb, 0.5 kb, and 0.3 kb long.

The 1.4 kb product (designated R10/1) and the 0.5 kb product (designated R10/2) were separated on a 3% agarose gel and purified using the Bresa-clean™ nucleic acid purification kit (Bresatec, Adelaide, S. Australia). These purified products were used as templates in further PCR reactions in order to generate a greater yield of product. PCR reactions were conducted exactly as described supra, except that 1 µl of purified PCR product (either RIO/1 or R10/2) was used as DNA template instead of 1 µl of the LIM1215 cDNA library.

The R10/1 PCR reaction produced two bands:

| | |
|---|---|
| Upper band | Size 1.4 kb (very faint) |
| Lower band | Size 0.3 kb (strong) designated 10/1 300 bp |

The R10/2 PCR reaction produced two bands:

| | |
|---|---|
| Upper band | Size 0.5 kb (strong) |
| Lower band | Size 0.3 kb (strong) designated 10/2 |

The 0.3 kb fragments (10/1 300bp and 10/2) were gel-purified as described above. Nucleotide sequencing of both fragments was conducted and the reverse complement of each sequence was found to encode a portion of the A33 N-terminal protein sequence.

The following precise primers to the A33 antigen cDNA sequence were then synthesized in order to amplify a precise 189 bp PCR product for use as a probe to screen the LIM1215 cDNA library.

Primer #1747 (A33wsense primer 1) 5'CCTGTCTG-GAGGCTGCCAGT (20mer) (SEQ ID NO: 19)

Primer #1748 (A33 antisense primer 1) 5'AGGTG-CAGGGCAGGGTGACA (20mer) (SEQ ID NO: 20)

The above primers were used in a standard PCR reaction as follows, and generated a product of the predicted size (189 bp).

Standard PCR Reaction Conditions

| | |
|---|---|
| 10/1-300 bp product | 1 µl |
| 10 × Taq buffer | 2 µl |
| 2.5 mM NTPs | 1.6 µl |
| 15 mM MgCl$_2$ | 2 µl |
| Primer #1747 (50 pmoles/µl) | 1 µl |
| Primer #1748 (50 pmoles/µl) | 1 µl |
| Water | 11 µl |
| Taq polymerase | 0.4 µl (added last) |
| | 20.0 µl |

Standard PCR program as follows:

| | |
|---|---|
| 1 | 95° C. × 5 min |
| 2 | 95° C. × 1 min |
| 3 | 55° C. × 1 min |
| 4 | 72° C. × 1 min |
| 5 | Go to (2) thirty times |
| 6 | 72° C. × 5 min |
| 7 | 4° C. hold |

The 189 bp product was separated on a 3% agarose gel and purified using the Bresa-clean™ kit. It was then radio-labelled with [α$^{32}$P]ATP and [α$^{32}$P]CTP to a specific activity of >10$^7$ dpm/µg DNA using well known random primer reaction and Klenow polymerase procedures and used to screen 800,000 clones of the LIM1215 cDNA library (standard procedures). After three rounds of screening thirteen purified A33 antigen cDNA clones were obtained, the longest of which was approximately 2.8 kb. See infra.

The labelled PCR probe was also used in Northern analysis and produced a strong hybridizing signal with a single species of mRNA of size approximately 2.8 kb in total RNA and poly (A)$^+$ enriched RNA from LIM1215 cells, suggesting that the 2.8 kb clone was likely to be close to full-length. Several clones were sequenced and all were found to encode the A33 antigen N-terminal protein sequence. The complete nucleotide sequence of a 2.6 kb clone (clone 11) is depicted in FIG. 16.

When one 2.6 kb cDNA clone was radiolabelled as described above (i.e., using [α$^{32}$P]ATP and [α$^{32}$P]CTP in the random primers reaction with Klenow polymerase) and used in Northern analysis, a strong signal of size approximately 2.8 kb was obtained with total RNA prepared from A33 antigen positive cell lines (LIM1215, LIM1899 and LIM1863) and normal human colonic epithelial tissue, but not with total RNA form A33 antigen negative cell lines (LIM2099, LIM2405, LIM2537).

The 319 amino acid translation protein product (A33 antigen) was deduced from nucleotide sequence of several 2.6 kb clones. It was predicted that protein translation is initiated at the second ATG from the 5' end in the cDNA sequence. This was deduced by reference to the Kozak consensus sequence (GCCC(R)CCATGG (SEQ ID NO: 21)) for initiation of translation. The deduced full length translation protein product comprises 319 amino acids, and has the following amino acid sequence (SEQ ID NO: 22)

```
Met Val Gly Lys Met Trp Pro Val Leu Trp Thr Leu Cys Ala Val Arg
                 5                  10                   15
Val Thr Val Asp Ala Ile Ser Val Glu Thr Pro Gln Asp Val Leu Arg
                20                  25                  30
Ala Ser Gln Gly Lys Ser Val Thr Leu Pro Cys Thr Tyr His Thr Ser
            35                  40                  45
Thr Ser Ser Arg Glu Gly Leu Ile Gln Trp Asp Lys Leu Leu Leu Thr
        50                  55                  60
His Thr Glu Arg Val Val Ile Trp Pro Phe Ser Asn Lys Asn Tyr Ile
65                  70                  75                  80
His Gly Glu Leu Tyr Lys Asn Arg Val Ser Ile Ser Asn Asn Ala Glu
                85                  90                  95
Gln Ser Asp Ala Ser Ile Thr Ile Asp Gln Leu Thr Met Ala Asp Asn
               100                 105                 110
Gly Thr Tyr Glu Cys Ser Val Ser Leu Met Ser Asp Leu Glu Gly Asn
            115                 120                 125
Thr Lys Ser Arg Val Arg Leu Leu Val Leu Val Pro Pro Ser Lys Pro
        130                 135                 140
Glu Cys Gly Ile Glu Gly Glu Thr Ile Ile Gly Asn Asn Ile Gln Leu
145                 150                 155                 160
Thr Cys Gln Ser Lys Glu Gly Ser Pro Thr Pro Gln Tyr Ser Trp Lys
                165                 170                 175
Arg Tyr Asn Ile Leu Asn Gln Glu Gln Pro Leu Ala Gln Pro Ala Ser
```

-continued

```
            180               185               190
Gly Gln Pro Val Ser Leu Lys Asn Ile Ser Thr Asp Thr Ser Gly Tyr
        195               200               205

Try Ile Cys Thr Ser Ser Asn Glu Glu Gly Thr Gln Phe Cys Asn Ile
        210               215               220

Thr Val Ala Val Arg Ser Pro Ser Met Asn Val Ala Leu Tyr Val Gly
225               230               235               240

Ile Ala Val Gly Val Val Ala Ala Leu Ile Ile Gly Ile Ile Ile
                245               250               255

Tyr Cys Cys Cys Cys Arg Gly Lys Asp Asp Asn Thr Glu Asp Lys Glu
            260               265               270

Asp Ala Arg Pro Asn Arg Glu Ala Tyr Glu Glu Pro Pro Glu Gln Leu
        275               280               285

Arg Glu Leu Ser Arg Glu Arg Glu Glu Glu Asp Asp Tyr Arg Gln Glu
        290               295               300

Glu Gln Arg Ser Thr Gly Arg Glu Ser Pro Asp His Leu Asp Gln
305               310               315
```

It is proposed that the protein contains a 21 amino acid hydrophobic leader sequence which is cleaved to produce a 298 amino acid mature protein with the known N-terminal corrresponding to amino acids 22–319 of SEQ ID NO: 22, i.e.:

```
Ile Ser Val Glu Thr Pro Gln Asp Val Leu Arg Ala Ser Gln Gly Lys
                5                 10                15

Ser Val Thr Leu Pro Cys Thr Tyr His Thr Ser Thr Ser Ser Arg Glu
            20                25                30

Gly Leu Ile Gln Trp Asp Lys Leu Leu Leu Thr His Thr Glu Arg Val
        35                40                45

Val Ile Trp Pro Phe Ser Asn Lys Asn Tyr Ile His Gly Glu Leu Tyr
    50                55                60

Lys Asn Arg Val Ser Ile Ser Asn Asn Ala Glu Gln Ser Asp Ala Ser
65                70                75                80

Ile Thr Ile Asp Gln Leu Thr Met Ala Asp Asn Gly Thr Tyr Glu Cys
            85                90                95

Ser Val Ser Leu Met Ser Asp Leu Glu Gly Asn Thr Lys Ser Arg Val
            100               105               110

Arg Leu Leu Val Leu Val Pro Pro Ser Lys Pro Glu Cys Gly Ile Glu
        115               120               125

Gly Glu Thr Ile Ile Gly Asn Asn Ile Gln Leu Thr Cys Gln Ser Lys
130               135               140

Glu Gly Ser Pro Thr Pro Gln Tyr Ser Trp Lys Arg Tyr Asn Ile Leu
145               150               155               160

Asn Gln Glu Gln Pro Leu Ala Gln Pro Ala Ser Gly Gln Pro Val Ser
                165               170               175

Leu Lys Asn Ile Ser Thr Asp Thr Ser Gly Tyr Tyr Ile Cys Thr Ser
            180               185               190

Ser Asn Glu Glu Gly Thr Gln Phe Cys Asn Ile Thr Val Ala Val Arg
        195               200               205

Ser Pro Ser Met Asn Val Ala Leu Tyr Val Gly Ile Ala Val Gly Val
        210               215               220

Val Ala Ala Leu Ile Ile Ile Gly Ile Ile Ile Tyr Cys Cys Cys Cys
```

```
225                 230                 235                 240

Arg Gly Lys Asp Asp Asn Thr Glu Asp Lys Glu Asp Ala Arg Pro Asn
                245                 250                 255

Arg Glu Ala Tyr Glu Glu Pro Pro Glu Gln Leu Arg Glu Leu Ser Arg
                260                 265                 270

Glu Arg Glu Glu Glu Asp Asp Tyr Arg Gln Glu Glu Gln Arg Ser Thr
        275                 280                 285

Gly Arg Glu Ser Pro Asp His Leu Asp Gln
    290                 295
```

The position of the first in-frame stop codon predicts a polypeptide chain, which has a $M_r$ of 33276. Based on a hydrophilicity plot constructed from the amino acid sequence, the molecule appears to have three portions: an extracellular region of 213 amino acids (which by sequence alignment of conserved residues appears to contain two immunoglobulin-like domains), a highly hydrophobic transmembrane domain of 24–27 amino acids, and a highly polar intracellular C-terminal tail. This general structure is suggestive of the molecule being involved in signal transduction.

The cDNA sequence starting at base pair 113 from the 5' end of clone 11, to base pair 1070 of clone 11, which encodes the 298 amino acid protein is as follows (SEQ ID NO: 23):

```
ATGGTGGGGA AGATGTGGCC TGTGTTGTGG ACACTCTGTG CAGTCAGGGT GACCGTCGAT

GCCATCTCTG TGGAAACTCC GCAGGACGTT CTTCGGGCTT CGCAGGGAAA GAGTGTCACC

CTGCCCTGCA CCTACCACAC TTCCACCTCC AGTCGAGAGG GACTTATTCA ATGGGATAAG

CTCCTCCTCA CTCATACGGA AAGGGTGGTC ATCTGGCCGT TTTCAAACAA AAACTACATC

CATGGTGAGC TTTATAAGAA TCGCGTCAGC ATATCCAACA ATGCTGAGCA GTCCGATGCC

TCCATCACCA TTGATCAGCT GACCATGGCT GACAACGGCA CCTACGAGTG TTCTGTCTCG

CTGATGTCAG ACCTGGAGGG CAACACCAAG TCACGTGTCC GCCTGTTGGT CCTCGTGCCA

CCCTCCAAAC CAGAATGCGG CATCGAGGGA GAGACCATAA TTGGGAACAA CATCCAGCTG

ACCTGCCAAT CAAAGGAGGG CTCACCAACC CCTCAGTACA GCTGGAAGAG GTACAACATC

CTGAATCAGG AGCAGCCCCT GGCCCAGCCA GCCTCAGGTC AGCCTGTCTC CCTGAAGAAT

ATCTCCACAG ACACATCGGG TTACTACATC TGTACCTCCA GCAATGAGGA GGGGACGCAG

TTCTGCAACA TCACGGTGGC CGTCAGATCT CCCTCCATGA ACGTGGCCCT GTATGTGGGC

ATCGCGGTGG GCGTGGTTGC AGCCCTCATT ATCATTGGCA TCATCATCTA CTGCTGCTGC

TGCCGAGGGA AGGACGACAA CACTGAAGAC AAGGAGGATG CAAGGCCGAA CCGGGAAGCC

TATGAGGAGC CACCAGAGCA GCTAAGAGAA CTTTCCAGAG AGAGGGAGGA GGAGGATGAC

TACAGGCAAG AAGAGCAGAG GAGCACTGGG CGTGAATCCC CGGACCACCT CGACCAGTGA
```

Comparison with available DNA and protein databases revealed that the protein consisting of the amino acid sequence sutra (SEQ ID NO: 22) was novel. However, analysis of available expressed sequence tag (EST) databases revealed 74% sequence similarity between part of the human A33 antigen cDNA (nucleotides 286–529) and a 249 base pair EST derived from the murine embryonal carcinoma cell line F9 (EMBL Accession No. MM88A09; DDBJ Accession No. D28657). In the likelihood that this EST corresponded to part of the murine homologue of the human A33 antigen cDNA, sense and antisense PCR primers (17mers) were designed to hybridize to the extremities of the EST clone, as follows:

Primer #1867 (F9 A33 sense) 5'TGACAAAGAAATA-CATC (SEQ ID NO: 24)

Primer #1868 (F9 A33 antisense) 5'TCTGGCTTG-GAGGGTGG (SEQ ID NO: 25)

These primers were used in the touchdowh PCR program described above to amplify a 218 bp product from a normal adult mouse colonic crypt cDNA library. See, e.g. J. Biol. Chem. 268: 27214–27225 (1993) for details on the murine cDNA library used. Briefly the cDNA was reverse transcribed from poly(A)+ enriched RNA purified from adult mouse colon crypt epithelium, and then cloned into the λgt-11 expression vector. This product was gel-purified and DNA sequencing demonstrated that this product closely corresponded to the F9 EST:

```
Seq 1  (SEQ ID NO: 26)           Seq 2  (SEQ ID NO: 27)
MM88A09 EST sequence(nucleic)    mouse colon CDNA (PCR
                                 product)
Seq 1
5'AGTATCTAACGAGTGCTGAGGTTGTCAAATGCCTCTATCACCATCGACCAGCTGACCATGGA Seq 2
5'AGTATCTAACGA-TGCTGAG-TTGTCAAATGCCTCTATCACCATCGACCAGCTGACCATGGA Seq 1
CGACAATGGCACCTACGAGTGCTCCGGTGTCACTGATGTCGGACCAGGATGTCAACGCCAA Seq 2
CGACAATGGCACCTACGAGTGCTCCG-TGTCACTGATGTCGGACCAGGATGTCAACGCCAA
```

Translation of the murine colonic PCR product revealed significant homology with part of the sequence of the A33 antigen (residues 64–104 of the cleaved molecule, residues 85–125 of SEQ ID NO: 22). The alignment between the predicted human and murine protein sequences is shown below:

Human (amino acids 85–125 of SEQ ID NO: 22)

```
85
Y K N R V S I S N N A E Q S D A S I T I D Q L T M A D N G T Y E C S V

S L M S D L
          125
```

Murine (SEQ ID NO: 28)

```
Y E N R V R V S N D A E L S N A S I T I D O L T M D D N G T Y E C S V

S L M S D Q
```

The F9 PCR product was radiolabelled ([α$^{32}$P]ATP and [α$^{32}$P] CTP as before) and used as a probe in Northern analysis of multiple murine tissue RNAs (from colonic crypts, small intestinal crypts, kidney, liver, brain, spleen, thymus, lung, pancreas, testis, heart, and thigh muscle). An intense band of approximately 2.6 kb in size was seen only in the lanes containing RNA prepared from colonic crypts and small intestinal crypts, with a very weak signal when testis and pancreas RNA were used. This close correspondence with the size of human A33 antigen mRNA, together with the alignment shown above and the restricted tissue expression, strongly suggested that the F9 clone encodes the murine homologue of the A33 antigen. In addition, these data suggest that the F9 EST contains errors and that the authentic sequence is better described by the sequence of the PCR product described herein.

The F9 PCR product was then used to screen the murine colonic crypt cDNA library described supra, for full length murine A33 cDNA clones. Standard methodologies were used, and twenty clones were identified, most of which contained A33 cDNA inserts of about 2.2 kb; however, two contained longer, 4.2 kb inserts. DNA sequencing was carried out on these two longer clones, and two of the 2.2 kb clones, using standard methods. The 3' sequence of the 4.2 kb clones did not correspond to A33 antigen cDNA, and sequence similarity searching of publicly available libraries using BLAST and FASTA algorithms showed that the 3'-end corresponded to cDNA for stomach, non-muscle $Ca^{2+}$ ATP-ase.

The 5'-end of all four clones was recognizable as an A33 antigen nucleotide sequence. Hence, the 4.2 kb clone comprises A33 cDNA at its 5'-end, and the stomach non-muscle $Ca^{2+}$ ATP-ase cDNA at its 3'-end. Sequencing of the 4.2 kb clones showed 2202 base pairs of A33 cDNA. The shorter clones contained 2122 base pairs of cDNA for the antigen. Translation of the longest ORE; predicts a 318 amino acid protein which is not complete at the —NH$_2$ terminus. It shows the same basic structure as the human antigen, and is highly homologous to it. A 20 amino acid hydrophobic leader sequence (missing the initiative methionine) is seen (compared to 21 for human), a V-set, a C2 set immunoglobulin like domain, a 24 amino acid hydrophobic transmembrane domain, and a 61 amino acid intracellular domain are presented. Further, the N-terminal region contains a consensus peptide cleavage site: ADA↓LTVET (SEQ ID NO: 29) which is similar to human cleavage site: ADA↓SVET (SEQ ID NO: 30), each of which produce a mature protein of 298 amino acids.

Overall analysis shows 71% similarity between murine and human sequences in the extracellular domain, 67% in the transmembrane domain, and 54% in the intracellular domain. The murine protein shows 4 potential N-linked glycosylation sites at positions 78, 91, 179 and 202, as compared to the human sequence, which has three potential sites at 91, 179 and 202.

The nucleotide and deduced amino acid sequences for the murine clone are set forth at SEQ ID NOS: 31 and 32. An alignment of the deduced amino acid sequences of human and murine sequences are set forth at FIG. 17.

EXAMPLE 17

A further set of experiments were carried out, using the protocols described supra, and the longest A33 antigen cDNA clone (clone 18) was found which also encoded A33. The nucleotide sequence of this clone is presented in SEQ ID NO: 33. This clone is slightly larger than that provided supra for clone 11, in that clone 18 is about 2.8 kilobases long, while clone 11, as indicated, is 2.6 kilobases long. In SEQ ID NO: 29, nucleotides 345 to 1302 appear to encode the amino acid sequence set forth in SEQ ID NO: 33.

EXAMPLE 18

As noted, supra, the A33 molecule is believed to be a glycoprotein, with N-linked glycosylation. Additional studies were carried out on relevant post-translational modifications to the antigen.

As reported, supra, the cell lines SW1222, LIM 1215, and COLO 205 are all A33 positive, while SW620 and MF-SH are A33 negative. All of these cell lines were metabolically labelled with $^3$H-palmitate, at 500 µCi/ml, then lysed with detergent, and the lysates were precipitated with A33 and FB5, as described supra. FB5, it will be recalled,. serves as a negative control. The precipitates were then subjected to SDS-PAGE analysis, as well as autoradiofluorography.

Figure 18A:
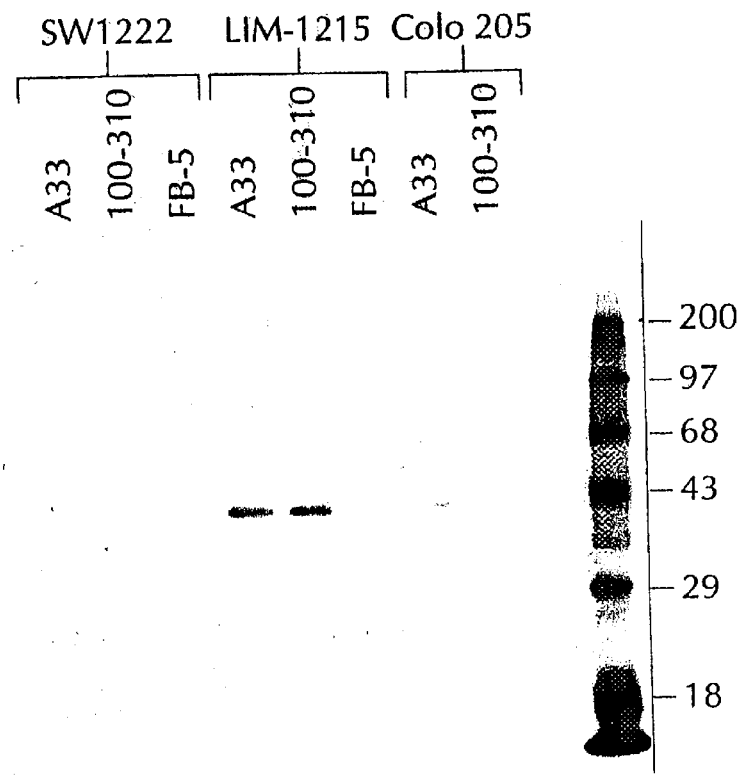
FIG. 18 shows that mAb A33 precipitated labelled A33 antigen, following labelling with palmitate.
Figure 18B:
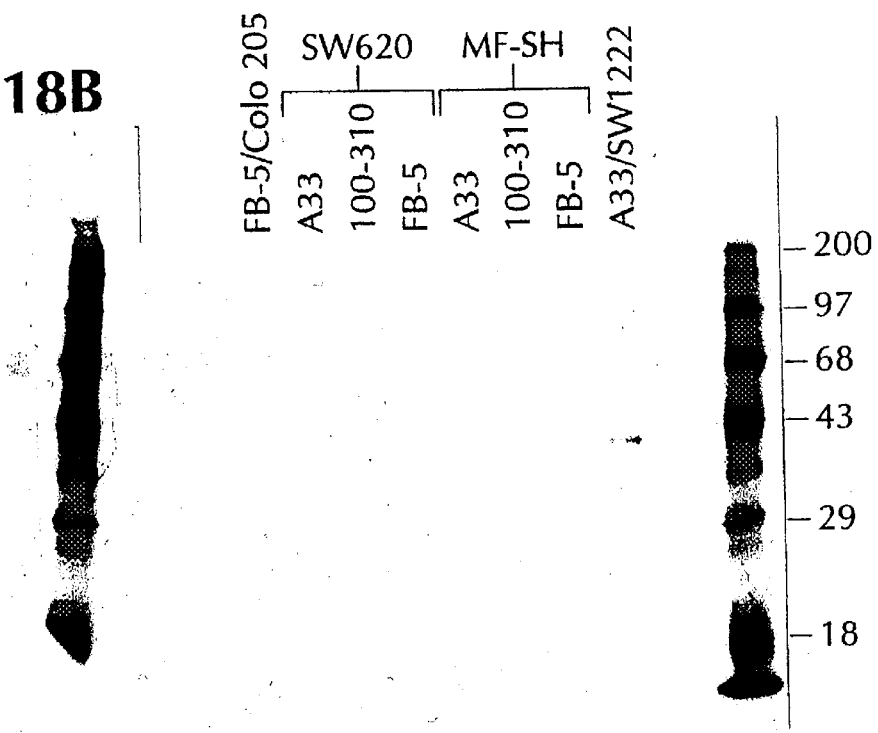
Figure 19B:
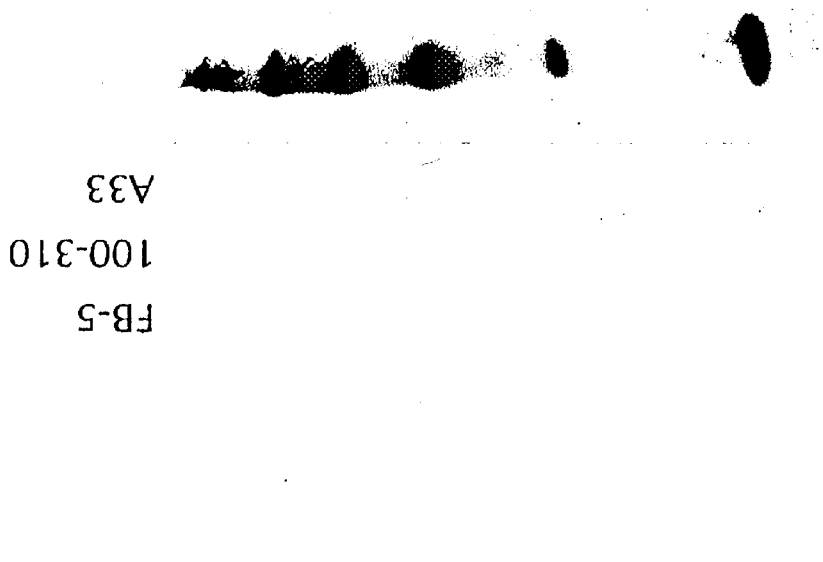
FIG. 19 depicts the abolition of staining when hydroxylamine was used.
Figure 19A:
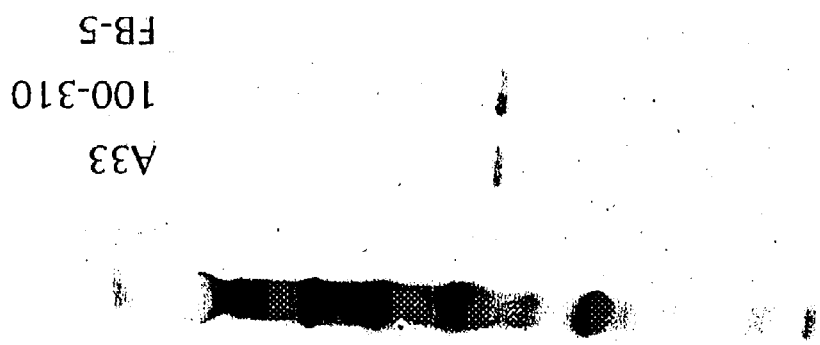

The results are shown in FIGS. 18 and 19. In FIG. 18, it will be seen that A33 $^3$H-palmitate labelled A33 antigen, with molecular weights at reduced and non-reduced conditions which were expected. The labelled precipitates were found in all three positive cells, but neither of the negative cells. FB5 was negative in all tests.

When the SDS gels were treated with 1M hydroxylamine (pH 7.5), before autoradiofluorography, staining was abolished, as FIG. 19 shows. This indicates that palmitate groups (acyls), are linked via thioesters. A $(CyS)_4$ domain is found in the molecule, and it is proposed that the palmitate is linked thereto.

The A33 antigen which has now been isolated, characterized and sequenced, can be used to diagnose cancer, colon cancer in particular which is characterized by the expression of the A33 antigen. For example, a sample suspected of containing colon cancer cells is contacted with an antibody specific for the A33 antigen or a fragment thereof, so that A33 protein/antibody complexes can be formed. If these complexes are present, a positive colon cancer diagnosis is indicated.

In addition, the A33 antigen can be used to identify ligands which bind to it (binding partners). The A33 antigen can be isolated, or recombinantly expressed, and used to screen biological sources, including tissue culture media, tissue extracts and cell lysates, for binding partners. Once a binding partner has been found, it is isolated and purified, and can be sequenced. This can be done with the use of a biosensor, in combination with affinity and other chromatographic techniques. Optionally, the A33 antigen can be tagged, to assist in immobilization of the antigen in a specific orientation onto the biosensor surface or affinity support. Identifying binding partners can be done utilizing techniques known to those skilled in the art. See, for example, Stitt et al., Cell, Vol. 80, pp. 661–670 (1995), Nice et al., J. Chromatoaraphy A., Vol. 660, pp. 169–185 (1994) and Bartley et al., Nature, Vol. 368, p. 558 (1994); Lachmann et al., Proc. Natl. Acad. Sci. USA 93: 2523–2527 (1993).

Further, the cDNA encoding A33 antigen has been described herein. This cDNA, including the untranslated portions at the 5' and 3' ends, easily facilitates the production of A33 antigen double-stranded cDNA molecules from tissues and cell lines expressing the A33 antigen, and A33 antigen genomic clones from genomic DNA. To do this, the A33 cDNA is used to design complementary primers for use in the technique of RT-PCR (reverse transcriptase-PCR), a standard procedure for the production of double-stranded cDNA molecules from mRNA templates. Further, the A33 cDNA can be used to design complementary primers for use in standard PCR reactions to amplify portions of the A33 antigen gene from genomic DNA templates.

It is possible that the A33 antigen resides in a novel family of related proteins. The A33 cDNA sequence described herein can be used to design specific and degenerate oligonucleotide primers for use in low stringency PCR reactions to amplify portions of cDNA and genomic DNA molecules encoding proteins related to the A33 antigen. In addition, the A33 cDNA can be used to design specific and degenerate oligonucleotide probes for the identification of members of the A33 antigen gene family by Southern analysis of genomic DNA under low stringency conditions.

These procedures utilizing A33 cDNA are standard procedures, known to those skilled in the art of molecular biology. See, for example, Molecular Cloning: A Laboratory Manual, 2nd edition, 1989 (eds. Sambrook J, Fritsch EF & Maniatis T) Cold Spring Harbor Laboratory Press, U.S.A., and Current Protocols in Molecular Biology Volumes I & II, 1989 (ed. Ausubel, FM) Greene Publishing Associates and Wiley-Interscience, U.S.A.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

SEQ ID NO: 31

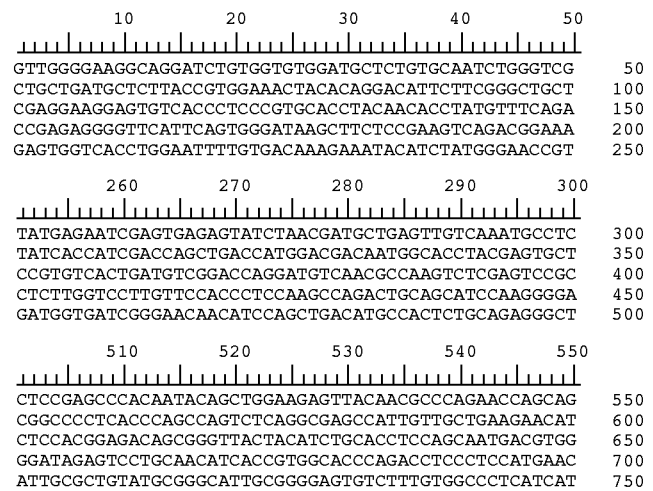

```
         10        20        30        40        50
         |         |         |         |         |
GTTGGGGAAGGCAGGATCTGTGGTGTGGATGCTCTGTGCAATCTGGGTCG     50
CTGCTGATGCTCTTACCGTGGAAACTACACAGGACATTCTTCGGGCTGCT    100
CGAGGAAGGAGTGTCACCCTCCCGTGCACCTACAACACCTATGTTTCAGA    150
CCGAGAGGGGTTCATTCAGTGGGATAAGCTTCTCCGAAGTCAGACGGAAA    200
GAGTGGTCACCTGGAATTTTGTGACAAAGAAATACATCTATGGGAACCGT    250

260       270       280       290       300
         |         |         |         |         |
TATGAGAATCGAGTGAGAGTATCTAACGATGCTGAGTTGTCAAATGCCTC    300
TATCACCATCGACCAGCTGACCATGGACGACAATGGCACCTACGAGTGCT    350
CCGTGTCACTGATGTCGGACCAGGATGTCAACGCCAAGTCTCGAGTCCGC    400
CTCTTGGTCCTTGTTCCACCCTCCAAGCCAGACTGCAGCATCCAAGGGGA    450
GATGGTGATCGGGAACAACATCCAGCTGACATGCCACTCTGCAGAGGGCT    500

510       520       530       540       550
         |         |         |         |         |
CTCCGAGCCCACAATACAGCTGGAAGAGTTACAACGCCCAGAACCAGCAG    550
CGGCCCCTCACCCAGCCAGTCTCAGGCGAGCCATTGTTGCTGAAGAACAT    600
CTCCACGGAGACAGCGGGTTACTACATCTGCACCTCCAGCAATGACGTGG    650
GGATAGAGTCCTGCAACATCACCGTGGCACCCAGACCTCCCTCCATGAAC    700
ATTGCGCTGTATGCGGGCATTGCGGGGAGTGTCTTTGTGGCCCTCATCAT    750
```

```
              760       770       780       790       800
              |||||||||||||||||||||||||||||||||||||||||||
CATCGGTGTCATTGTCTACTGCTGCTGCTGCCGGGAAAAGGATGACAAAG    800
ATCAAGACAGGGAGGATGCGCGGCCGAACCGAGCAGCTTACCAAGTGCCT    850
AAAAAGGAGCAGAAAGAAATTTCCAGAGGGCGGGAAGACGAAGATGACCA    900
CAGACATGAGGATCGGTGGAGCTCGGGGCGTAGCACTCCAGACCAGCCTT    950
TCCAATGAAGGAGCCTTCTGCCCAGCGGGGAGAGGGGGGAGGTCTAGGGC   1000
              1010      1020      1030      1040      1050
              |||||||||||||||||||||||||||||||||||||||||||
CCAGGCTCCTGCTCTGGCCACCCTTCTCCCCAGCCCCATAGTCCTGCTCC   1050
TCCCCCCAGGCATTGGTGGAGCACTTCTTTCTGTGTATCTGCCTCAGGGG   1100
CGCATCACTGGCCTGGCTACTGACGTCCTACCTGATGACCACTGAAAGGA   1150
CCCTTCCTCATTGCTAAATCTGACTCAGGGTCTGGCCTTCTCCCTAGACC   1200
AGACAGCATCCTCTGCCTCTCTTACGGCTGGCAGGGCCTCCTAGAATCTC   1250
              1260      1270      1280      1290      1300
              |||||||||||||||||||||||||||||||||||||||||||
GGCACGATGCAGGGCTGCTTCTGTTCCAAGCTCGCCATACAGGCAAGCGC   1300
CAGCTTCAGCACCAGTTTCAGAAGGTGGGAGTCTGCCCTGCCTCACCATG   1350
CCCGACACTCAGAGGAGAACCAGTGATGGGCCTGCACGCAATATTTTGTT   1400
GAATGAAGGGAAGAAATCAACGATAAGGTGTAGTTTCTGTGATTTACCCA   1450
GCTTAATTGCGCCCCCCCCCCCCCATGCTGAGGGGCCACGGTGGCCTCCA   1500
              1510      1520      1530      1540      1550
              |||||||||||||||||||||||||||||||||||||||||||
GCGTCCCCCTCTGCTCCATCTCCCACCATGGCGTTTCTGTTCCTGGACAC   1550
ACACCTTCTTAGGACTTCTCCAAACACAGTTCCATCTCTGCCTGTCAAGG   1600
GCCTGCCTGTCCTTAGAACTCACTAGTCTTGGATCCCCAAATCTTTCTTA   1650
ATCCTGTGACTGCTAACACACCAGGAGGCAATGAAGTCACTTTGTCCCAC   1700
ACCTAGACCTGGGCTGCATGCAAGGCCATCAGAGCTACACTTCCTGCTGT   1750
              1760      1770      1780      1790      1800
              |||||||||||||||||||||||||||||||||||||||||||
GTTAGAGTAGGTGCCCTGGAGCAAGGTCTGGATCTTGGAGCCTGGCAGCC   1800
TCAACTGGGGACTTGCTCTCATGGACAGTGCTTTGCCTCCTGGGTGTGAC   1850
TTGGGACACCTGGTGACTCCACCCAAGCCCCGTGTTAGTCTGGCTAGGTG   1900
GGCAGACTGATTTACAATGAACACAGACAAAAGCTTACTTCCCTCGCACC   1950
TGCCAGCTGCCCTGCCTGCCGCAGCCTCCCCTTTCCATTACTATCCAGGA   2000
              2010      2020      2030      2040      2050
              |||||||||||||||||||||||||||||||||||||||||||
CTCAGGCCAGATGGGCTGCTCCAAATGTGTTTTACTACTGGATAAACCTT   2050
TCTGGATCACCAGAAAAGCAACTGTATCAATCCCTTCCCTCCTCTGATTT   2100
TATGTACACATATATTTTATATACTTGGCTAAATTCTTTGTTTCAATCAA   2150
AATGTTTCTTTATCAATAAAGTTACTGGTGGAAATTCAAAAAAAAAAAA   2200
AA                                                  2202

SEQ ID NO: 32
                                   I-318
              10        20        30        40
              |||||||||||||||||||||||||||||||||||||||||||
LGKAGSVVWMLCAIWVAADALTVETTQDILRAARGRSVTL              40
PCTYNTYVSDREGFIQWDKLLRSQTERVVTWNFVTKKYIY              80
GNRYENRVRVSNDAELSNASITIDQLTMDONGTYECSVSL             120
MSDQDVNAKSRVRLLVLVPPSKPDCSIQGEMVIGNNIQLT             160
CHSAEGSPSPQYSWKSYNAQNQQRPLTQPVSGEPLLLKNI             200
              210       220       230       240
              |||||||||||||||||||||||||||||||||||||||||||
STETAGYYICTSSNDVGIESCNITVAPRPPSMNIALYAGI              240
AGSVFVALIIIGVIVYCCCCREKDDKDQDREDARPNRAAY              280
QVPKKEDKEISRGREDEDDHRHEDRWSSGRSTPDQPFQ                319
```

NUCLEOTIDE SEQUENCE OF MURINE A33 ANTIGEN

```
CTACCCCTTTGTGAGCAGTCTAGGACTTTGTACACCTGTTAAGTAGGGAGAAGGCAGGGGAGGTGGCTGGTTTAAGGGGA     80  SEQ ID NO: 33

ACTTGAGGGAAGTAGGGAAGACTCCTCTTGGGACCTTTGGAGTAGGTGACACATGAGCCCAGCCCCAGCTCACCTGCCAA    160

TCCAGCTGAGGAGCTCACCTGCCAATCCAGCTGAGGCTGGGCAGAGGTGGGTGAGAAGAGGGAAAATTGCAGGGACCTCC    240

AGTTGGGCCAGGCCAGAAGCTGCTGTAGCTTTAACCAGACAGCTCAGACCTGTCTGGAGGCTGCCAGTGACAGGTTAGGT    242

TTAGGGCAGAGAAGAAGCAAGACCATGGTGGGAAGATGTGGCCTGTGTTGTGGACACTCTGTGCAGTCAGGGTGACCGT    400

CGATGCCATCTCTGTGGAAACTCCGCAGGACGTTCTTCGGGCTTCGCAGGGAAAGAGTGTCACCCTGCCCTGCACCTACC    480
```

```
ACACTTCCACCTCCAGTCGAGAGGGACTTATTCAATGGGATAAGCTCCTCCTCACTCATACGGAAAGGGTGGTCATCTGG   560
CCGTTTTCAAACAAAAACTACATCCATGGTGAGCTTTATAAGAATCGCGTCAGCATATCCAACAATGCTGAGCAGTCCGA   640
TGCCTCCATCACCATTGATCAGCTGACCATGGCTGACAACGGCACCTACGAGTGTTCTGTCTCGCTGATGTCAGACCTGG   720
AGGGCAACACCAAGTCACGTGTCCGCCTGTTGGTCCTCGTGCCACCCTCCAAACCAGAATGCGGCATCCAGGGAGAGACC   800
ATAATTGGGAACAACATCCAGCTGACCTGCCAATCAAAGGAGGGCTCACCAACCCCTCAGTACAGCTGGAAGAGGTACAA   880
CATCCTGAATCAGGAGCAGCCCCTGGCCCAGCCAGCCTCAGGTCAGCCTGTCTCCCTGAAGAATATCTCCACAGACACAT   960
CGGGTTACTACATCTGTACCTCCAGCAATGAGGAGGGACGCAGTTCTGCAACATCACGGTGGCCGTCAGATCTCCCTCC  1040
ATGAACGTGGCCCTGTATGTGCGCATCGCGGTGGGCGTGGTTGCAGCCCTCATTATCATTGGCATCATCATCTACTGCTG  1120
CTGCTGCCAGGGAAGGACGACAACACTGAAGACAAGGACGATGCAAGGCCGAACCGGGAAGCCTATGAGGAGCCACCAG  1200
AGCAGCTAAGAGAACTTTCCAGAGAGAGGGAGGAGGAGGATGACTACAGGCAAGAAGAGCAGAGGAGCACTGGGCGTGAA  1280
TCCCCGGACCACCTCGACCAGTGACAGGCCAGCAGCAGAGGGCGGCGGAGGAAGGGTTAGGGGTTCATTCTCCCGCTTCC  1320
TGGCCTCCCTTCTCCTTTCTAAGCCCTGTTCTCCTGTCCCTCCATCCCAGACATTGATGGGGACATTTCTTCCCCAGTGT  1440
CAGCTGTGGGGAACATGGCTGGCCTGGTAAGGGGGTCCCTGTGCTGATCCTGCTGACCTCACTGTCCTGTGAAGTAACCC  1520
CTCCTGGCTGTGACACCTGGTGCGGGCCTGGCCCTCACTCAAGACCAGGCTGCAGCCTCCACTTCCCTCGTAGTTGGCAG  1600
GAGCTCCTGGAAGCACAGCGCTGAGCATGGGCGCTCCCACTCAGAACTCTCCAGGGAGGCGATGCCAGCCTTGGGGGGT  1680
GGGGGCTGTCCTGCTCACCTGTGTGCCCAGCACCTGGAGGGGCACCAGGTGGAGGGTTTGCACTCCACACATCTTTCTTG  1760
AATGAATGAAAGAATAAGTGAGTATGCTTGGCCCCTGCATTGGCCTGGCCTCCAGCTCCCACTCCCTTTCCAACCTCACT  1840
TCCCGTAGCTGCCAGTATGTTCCAAACCCTCCTGGGAAGGCCACCTCCCACTCCTGCTGCACAGGCCCTGGGGAGCTTTT  1920
GCCCACACACTTTCCATCTCTGCCTGTCAATATCGTACCTGTCCCTCCAGGCCCATCTCAAATCACAAGGATTTCTCTAA  2000
CCCTATCCTAATTGTCCACATACGTGGAAACAATCCTGTTACTCTGTCCCACGTGGAATCATGGGCCACAAGGCACAGTC  2090
TTCTGAGCGAGTGCTCTCACTGTATTAGAGCGCCAGCTCCTTGGGGCAGGGCCTGGGCCTCATGGCTTTTGCTTTCCCTG  2160
AAGCCCTAGTAGCTGGCGCCCATCCTAGTGGGCACTTAAGCTTAATTGGGGAAACTGCTTTGATTGGTTGTGCCTTCCCT  2240
TCTCTGGTCTCCTTGAGATGATCGTAGACACAGGGATGATTCCCACCCAAACCCACGTATTCATTCAGTGAGTTAAACAC  2320
GAATTGATTTAAAGTGAACACACACAAGGGAGCTTGCTTGCAGATGGTCTGAGTTCTTGTGTCCTGGTAATTCCTCTCCA  2400
GGCCAGAATAATTGGCATGTCTCCTCAACCCACATGGGGTTCCTGGTTGTTCCTGCATCCCGATACCTCAGCCCTCGCCC  2480
TGCCCAGCCCATTTGGGCTCTGGTTTTCTGGTGGGGCTGTCCTGCTGCCCTCCCACAGCCTCCTTCTGTTTGTCGAGCAT  2520
TTCTTCTACTCTTGAGAGCTCAGGCAGCGTTAGGGCTGCTTAGGTCTCATGGACCACTGGCTGGTCTCACCCAACTGCAG  2640
TTTACTATTGCTATCTTTTCTGGATGATCAGAAAAATAATTCCATAAATCTATTGTCTACTTGCGATTTTTAAAAAATG  2720
TATATTTTTATATATATTGTTAAATCCTTTGCTTCATTCCAAATGCTTTCAGTAATAATAAAATTGTGGGTGGAAAAAAA  2800
AAA                                                                              2803
```

---

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
       (A) LENGTH: 38 amino acids
       (B) TYPE: amino acid
       (D) TOPOLOGY: linear

```
        (xi) SEQUENCE DESCRIPTION: SEQ ID NO: 1:

Xaa Ser Val Glu Thr Pro Gln Asp Val Leu Arg Ala Ser Gln Gly Lys
                  5                  10                  15

Ser Val Thr Leu Pro Xaa Thr Tyr His Thr Ser Xaa Xaa Xaa Arg Glu
             20                  25                  30

Gly Leu Ile Gln Trp Asp
         35

(2) INFORMATION FOR SEQ ID NO: 2:

(i) SEQUENCE CHARACTERISTICS:
         (A) LENGTH: 11 amino acids
         (B) TYPE: amino acid
         (D) TOPOLOGY: linear (xi) SEQUENCE DESCRIPTION: SEQ ID NO: 2:

Glu Ala Tyr Glu Glu Pro Pro Glu Gln Leu Arg
                  5                  10

(2) INFORMATION FOR SEQ ID NO: 3:

(i) SEQUENCE CHARACTERISTICS:
         (A) LENGTH: 9 amino acids
         (B) TYPE: amino acid
         (D) TOPOLOGY: linear (xi) SEQUENCE DESCRIPTION: SEQ ID NO: 3:

Val Val Ile Trp Pro Phe Ser Asn Lys
                  5

(2) INFORMATION FOR SEQ ID NO: 4:

(i) SEQUENCE CHARACTERISTICS:
         (A) LENGTH: 40 amino acids
         (B) TYPE: amino acid
         (D) TOPOLOGY: linear (xi) SEQUENCE DESCRIPTION: SEQ ID NO: 4:

Ile Ser Val Glu Thr Pro Gln Asp Val Leu Arg Ala Ser Gln Gly Lys
                  5                  10                  15

Ser Val Thr Leu Pro Xaa Thr Tyr His Thr Ser Thr Ser Ser Arg Glu
             20                  25                  30

Gly Leu Ile Gln Trp Asp Lys Leu
         35                  40

(2) INFORMATION FOR SEQ ID NO: 5:

(i) SEQUENCE CHARACTERISTICS:
         (A) LENGTH: 30 amino acids
         (B) TYPE: amino acid
         (D) TOPOLOGY: linear (xi) SEQUENCE DESCRIPTION: SEQ ID NO: 5:

Asp Val Leu Arg Ala Ser Gln Gly Lys Ser Val Thr Leu Pro Cys Thr
                  5                  10                  15

Tyr His Thr Ser Thr Ser Ser Arg Glu Gly Leu Ile Gln Trp
             20                  25                  30

(2) INFORMATION FOR SEQ ID NO: 6:

(i) SEQUENCE CHARACTERISTICS:
         (A) LENGTH: 39 amino acids
         (B) TYPE: amino acid
         (D) TOPOLOGY: linear
```

(xi) SEQUENCE DESCRIPTION: SEQ ID NO: 6:

Asp Lys Leu Leu Leu Thr His Thr Glu Arg Val Val Ile Trp Pro Phe
                 5                  10                 15

Ser Asn Lys Asn Tyr Ile His Gly Glu Leu Tyr Lys Asn Arg Val Ser
            20                  25                  30

Ile Ser Asn Asn Ala Glu Gln
        35

(2) INFORMATION FOR SEQ ID NO: 7:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 7:

Glu Leu Tyr Lys Asn Arg Val Ser Ile Ser Asn Asn Ala Glu Gln
                 5                  10                 15

(2) INFORMATION FOR SEQ ID NO: 8:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO: 8:

Asp Xaa Gly Thr Tyr Glu Cys Ser Val Ser Leu Met
                 5                  10

(2) INFORMATION FOR SEQ ID NO: 9:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 9:

Ile Gln Leu Thr Cys Gln Ser Lys Glu Gly Ser Pro Thr Pro Gln Tyr
                 5                  10                 15

(2) INFORMATION FOR SEQ ID NO: 10:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO: 10:

Leu Val Leu Val Pro Pro Ser Lys Pro Glu Cys Gly Ile Glu Gly Glu
                 5                  10                 15

Thr Ile Ile Gly Asn
         20

(2) INFORMATION FOR SEQ ID NO: 11:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO: 11:

Ile Leu Asn Gln Glu Gln Pro Leu Ala Gln Pro Ala Ser Gly Gln Pro
                 5                  10                 15

Val (2) INFORMATION FOR SEQ ID NO: 12

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 12

ARYTTRTCCC ACTGAAT                                    17

(2) INFORMATION FOR SEQ ID NO: 13

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 13

ARYTTRTCCC ATTGAAT                                    17

(2) INFORMATION FOR SEQ ID NO: 14

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 14

ARYTTRTCCC ACTGGAT                                    17

(2) INFORMATION FOR SEQ ID NO: 15

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 15

ARYTTRTCCC ATTGGAT                                    17

(2) INFORMATION FOR SEQ ID NO: 16

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 16

ARYTTRTCCC ACTGTAT                                    17

(2) INFORMATION FOR SEQ ID NO: 17

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 17

ARYTTRTCCC ATTGTAT                                                  17

(2) INFORMATION FOR SEQ ID NO: 18

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 18

CGAGGTCGAC GGTATCG                                                  17

(2) INFORMATION FOR SEQ ID NO: 19

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 19

CCTGTCTGGA GGCTGCCAGT                                               20

(2) INFORMATION FOR SEQ ID NO: 20

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 20

AGGTGCAGGG CAGGGTGACA                                               20

(2) INFORMATION FOR SEQ ID NO: 21

(i) SEQUENCE CHARACTERISTICS:
        (A) LENGTH: 11 nucleotides
        (B) TYPE: nucleic acid
        (C) STRANDEDNESS: single
        (D) TOPOLOGY: linear (xi) SEQUENCE DESCRIPTION: SEQ ID NO: 21

GCCCRCCATG G                                                        11

(2) INFORMATION FOR SEQ ID NO: 22

(i) SEQUENCE CHARACTERISTICS:
        (A) LENGTH: 319 amino acids
        (B) TYPE: amino acid
        (D) TOPOLOGY: linear (xi) SEQUENCE DESCRIPTION: SEQ ID NO: 22

Met Val Gly Lys Met Trp Pro Val Leu Trp Thr Leu Cys Ala Val Arg
                 5                  10                  15

Val Thr Val Asp Ala Ile Ser Val Glu Thr Pro Gln Asp Val Leu Arg
             20                  25                  30

Ala Ser Gln Gly Lys Ser Val Thr Leu Pro Cys Thr Tyr His Thr Ser
         35                  40                  45

Thr Ser Ser Arg Glu Gly Leu Ile Gln Trp Asp Lys Leu Leu Leu Thr
     50                  55                  60

His Thr Glu Arg Val Val Ile Trp Pro Phe Ser Asn Lys Asn Tyr Ile
 65                  70                  75                  80

His Gly Glu Leu Tyr Lys Asn Arg Val Ser Ile Ser Asn Asn Ala Glu
              85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
            115                 120                 125

Thr Lys Ser Arg Val Arg Leu Leu Val Leu Val Pro Pro Ser Lys Pro
        130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
        195                 200                 205

Tyr Ile Cys Thr Ser Ser Asn Glu Glu Gly Thr Gln Phe Cys Asn Ile
    210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Ile Gly Ile Ile Ile
                245                 250                 255

Tyr Cys Cys Cys Cys Arg Gly Lys Asp Asp Asn Thr Glu Asp Lys Glu
            260                 265                 270

Asp Ala Arg Pro Asn Arg Glu Ala Tyr Glu Glu Pro Pro Glu Gln Leu
        275                 280                 285

Arg Glu Leu Ser Arg Glu Arg Glu Glu Asp Asp Tyr Arg Gln Glu
    290                 295                 300

Glu Gln Arg Ser Thr Gly Arg Glu Ser Pro Asp His Leu Asp Gln
305                 310                 315

(2) INFORMATION FOR SEQ ID NO: 23

(i) SEQUENCE CHARACTERISTICS:
        (A) LENGTH: 960 nucleotides
        (B) TYPE: nucleic acid
        (C) STRANDEDNESS: single
        (D) TOPOLOGY: linear (xi) SEQUENCE DESCRIPTION: SEQ ID NO: 23

ATGGTGGGGA AGATGTGGCC TGTGTTGTGG ACACTCTGTG CAGTCAGGGT GACCGTCGAT    60

GCCATCTCTG TGGAAACTCC GCAGGACGTT CTTCGGGCTT CGCAGGGAAA GAGTGTCACC   120

CTGCCCTGCA CCTACCACAC TTCCACCTCC AGTCGAGAGG GACTTATTCA ATGGGATAAG   180

CTCCTCCTCA CTCATACGGA AAGGGTGGTC ATCTGGCCGT TTTCAAACAA AAACTACATC   240

CATGGTGAGC TTTATAAGAA TCGCGTCAGC ATATCCAACA ATGCTGAGCA GTCCGATGCC   300

TCCATCACCA TTGATCAGCT GACCATGGCT GACAACGGCA CCTACGAGTG TTCTGTCTCG   360

CTGATGTCAG ACCTGGAGGG CAACACCAAG TCACGTGTCC GCCTGTTGGT CCTCGTGCCA   420

CCCTCCAAAC CAGAATGCGG CATCGAGGGA GAGACCATAA TTGGGAACAA CATCCAGCTG   480

ACCTGCCAAT CAAAGGAGGG CTCACCAACC CCTCAGTACA GCTGGAAGAG GTACAACATC   540

CTGAATCAGG AGCAGCCCCT GGCCCAGCCA GCCTCAGGTC AGCCTGTCTC CCTGAAGAAT   600

ATCTCCACAG ACACATCGGG TTACTACATC TGTACCTCCA GCAATGAGGA GGGGACGCAG   660

TTCTGCAACA TCACGGTGGC CGTCAGATCT CCCTCCATGA ACGTGGCCCT GTATGTGGGC   720

```
ATCGCGGTGG GCGTGGTTGC AGCCCTCATT ATCATTGGCA TCATCATCTA CTGCTGCTGC      780

TGCCGAGGGA AGGACGACAA CACTGAAGAC AAGGAGGATG CAAGGCCGAA CCGGGAAGCC      840

TATGAGGAGC CACCAGAGCA GCTAAGAGAA CTTTCCAGAG AGAGGGAGGA GGAGGATGAC      900

TACAGGCAAG AAGAGCAGAG GAGCACTGGG CGTGAATCCC CGGACCACCT CGACCAGTGA      960

(2) INFORMATION FOR SEQ ID NO: 24

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 24

TGACAAAGAA ATACATC                                                     17

(2) INFORMATION FOR SEQ ID NO: 25

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 25

TCTGGCTTGG AGGGTGG                                                     17

(2) INFORMATION FOR SEQ ID NO: 26

(i) SEQUENCE CHARACTERISTICS:
        (A) LENGTH: 123 nucleotides
        (B) TYPE: nucleic acid
        (C) STRANDEDNESS: single
        (D) TOPOLOGY: linear (xi) SEQUENCE DESCRIPTION: SEQ ID NO: 26

AGTATCTAAC GAGTGCTGAG GTTGTCAAAT GCTGACCATG GACGACAATG GCACCTACGA       60

GTGCTCCGGT GTCACTGATG GCCTCTATCA CCATCGACCA TCGGACCAGG ATGTCAACGC      120

CAA                                                                   123

(2) INFORMATION FOR SEQ ID NO: 27

(i) SEQUENCE CHARACTERISTICS:
        (A) LENGTH: 120 nucleotides
        (B) TYPE: nucleic acid
        (C) STRANDEDNESS: single
        (D) TOPOLOGY: linear (xi) SEQUENCE DESCRIPTION: SEQ ID NO: 27

AGTATCTAAC GATGCTGAGT TGTCAAATGC CTCTATCAGC TGACCATGGA CGACAATGGC       60

ACCTACGAGT GCTCCGTGTC ACTGATGCCA TCGACCATCG GACCAGGATG TCAACGCCAA     120

(2) INFORMATION FOR SEQ ID NO: 28

(i) SEQUENCE CHARACTERISTICS:
        (A) LENGTH: 41 amino acids
        (B) TYPE: amino acid
        (D) TOPOLOGY: linear (xi) SEQUENCE DESCRIPTION: SEQ ID NO: 28

Tyr Glu Asn Arg Val Arg Val Ser Asn Asp Ala Glu Lys Ser Asn
                 5                  10                  15
```

```
Ala Ser Ile Thr Ile Asp Gln Lys Thr Met Asp Asp Asn Gly Thr
            20                  25                  30

Tyr Glu Cys Ser Val Ser Leu Met Ser Asp Gln
            35                  40
```

(2) INFORMATION FOR SEQ ID NO: 29

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 29

```
Ala Asp Ala Leu Thr Val Glu Thr
             5
```

(2) INFORMATION FOR SEQ ID NO: 30

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 30

```
Ala Asp Ala Ile Ser Val Glu Thr
             5
```

(2) INFORMATION FOR SEQ ID NO: 31

(i) SEQUENCE CHARACTERISTICS:
        (A) LENGTH: 2565 nucleotides
        (B) TYPE: nucleic acid
        (C) STRANDEDNESS: single
        (D) TOPOLOGY: linear (xi) SEQUENCE DESCRIPTION: SEQ ID NO: 31

```
GGGACTCCAG TTGGGCCAGG CCAGAAGCTG CTGTAGCTTT AACCAGACAG CTCAGACCTG    60
TCTGGAGGCT GCCAGTGACA GGTTAGGTTT AGGGCAGAGA AGAAGCAAGA CCATGGTGGG   120
GAAGATGTGG CCTGTGTTGT GGACACTCTG TGCAGTCAGG GTGACCGTCG ATGCCATCTC   180
TGTGGAAACT CCGCAGGACG TTCTTCGGGC TTCGCAGGGA AAGAGTGTCA CCCTGCCCTG   240
CACCTACCAC ACTTCCACCT CCAGTCGAGA GGGACTTATT CAATGGGATA AGCTCCTCCT   300
CACTCATACG GAAAGGGTGG TCATCTGGCC GTTTTCAAAC AAAAACTACA TCCATGGTGA   360
GCTTTATAAG AATCGCGTCA GCATATCCAA CAATGCTGAG CAGTCCGATG CCTCCATCAC   420
CATTGATCAG CTGACCATGG CTGACAACGG CACCTACGAG TGTTCTGTCT CGCTGATGTC   480
AGACCTGGAG GGCAACACCA AGTCACGTGT CCGCCTGTTG GTCCTCGTGC CACCCTCCAA   540
ACCAGAATGC GGCATCGAGG GAGAGACCAT AATTGGGAAC AACATCCAGC TGACCTGCCA   600
ATCAAAGGAG GGCTCACCAA CCCCTCAGTA CAGCTGGAAG AGGTACAACA TCCTGAATCA   660
GGAGCAGCCC CTGGCCCAGC CAGCCTCAGG TCAGCCTGTC TCCCTGAAGA ATATCTCCAC   720
AGACACATCG GGTTACTACA TCTGTACCTC CAGCAATGAG GAGGGACGC AGTTCTGCAA   780
CATCACGGTG GCCGTCAGAT CTCCCTCCAT GAACGTGGCC CTGTATGTGG GCATCGCGGT   840
GGGCGTGGTT GCAGCCCTCA TTATCATTGG CATCATCATC TACTGCTGCT GCTGCCGAGG   900
GAAGGACGAC AACACTGAAG ACAAGGAGGA TGCAAGGCCG AACCGGGAAG CCTATGAGGA   960
GCCACCAGAG CAGCTAAGAG AACTTTCCAG AGAGAGGGAG GAGGAGGATG ACTACAGGCA  1020
AGAAGAGCAG AGGAGCACTG GGCGTGAATC CCCGGACCAC CTCGACCAGT GACAGGCCAG  1080
```

```
CAGCAGAGGG CGGCGGAGGA AGGGTTAGGG GTTCATTCTC CCGCTTCCTG GCCTCCCTTC    1140

TCCTTTCTAA GCCCTGTTCT CCTGTCCCTC CATCCCAGAC ATTGATGGGG ACATTTCTTC    1200

CCCAGTGTCA GCTGTGGGGA ACATGGCTGG CCTGGTAAGG GGGTCCCTGT GCTGATCCTG    1260

CTGACCTCAC TGTCCTGTGA AGTAACCCCT CCTGGCTGTG ACACCTGGTG CGGGCCTGCC    1320

CTCACTCAAG ACCAGGCTGC AGCCTCCACT TCCCTCGTAG TTGGCAGGAG CTCCTGGAGA    1380

GCACAGCGCT GAGCATGGGG CGCTCCCACT CAGAACTCTC CAGGGAGGCG ATGCCAGCCT    1440

TGGGGGGTGG GGGCTGTCCT GCTCACCTGT GTGCCCAGCA CCTGGAGGGG CACCAGGTGG    1500

AGGGTTTGCA CTCCACACAT CTTTCTTGAA TGAATGAAAG AATAAGTGAG TATGCTTGGG    1560

CCCTGCATTG GCCTGGCCTC CAGCTCCCAC TCCCTTTCCA ACCTCACTTC CCGTAGCTGC    1620

CAGTATGTTC CAAACCCTCC TGGGAAGGCC ACCTCCCACT CCTGCTGCAC AGGCCCTGGG    1680

GAGCTTTTGC CCACACACTT TCCATCTCTG CCTGTCAATA TCGTACCTGT CCCTCCAGGC    1740

CCATCTCAAA TCACAAGGAT TTCTCTAACC CTATCCTAAT TGTCCACATA CGTGGAAACA    1800

ATCCTGTTAC TCTGTCCCAC GTCCAATCAT GGGCCACAAG GCACAGTCTT CTGAGCGAGT    1860

GCTCTCACTG TATTAGAGCG CCAGCTCCTT GGGGCAGGGC CTGGGCCTCA TGGCTTTTGC    1920

TTTCCCTGAA GCCCTAGTAG CTGGCGCCCA TCCTAGTGGG CACTTAAGCT TAATTGGGGA    1980

AACTGCTTTG ATTGGTTGTG CCTTCCCTTC TCTGGTCTCC TTGAGATGAT CGTAGACACA    2040

GGGATGATTC CCACCCAAAC CCACGTATTC ATTCAGTGAG TTAAACACGA ATTGATTTAA    2100

AGTGAACACA CACAAGGGAG CTTGCTTGCA GATGGTCTGA GTTCTTGTGT CCTGGTAATT    2160

CCTCTCCAGG CCAGAATAAT TGGCATGTCT CCTCAACCCA CATGGGGTTC CTGGTTGTTC    2220

CTGCATCCCG ATACCTCAGC CCTGGCCCTG CCCAGCCCAT TTGGGCTCTG GTTTTCTGGT    2280

GGGNCTGTCC TGCTGCCCTC CCACNAGCCT CCTTCTGTTT GTCGAGCATT TCTTCTACTC    2340

TTNAGAGCTC AGGCAGCGTT AGGGCTGCTT AGGTCTCATG GACCAGTGGC TGGTCTCACC    2400

CAACTGCAGT TTACTATTGC TATCTTTTCT GGATGATCGA AAAAATAATT CCATAAATCT    2460

ATTGTCTACT TGCGATTTTT TAAAAAATGT ATATTTTTAT ATATATTGTT AAATCCTTTG    2520

CTTCATTCCA AATGCTTTCA GTAATAATAA AATTGTGGGT GGAAA                   2565
```

(2) INFORMATION FOR SEQ ID NO: 32

(i) SEQUENCE CHARACTERISTICS:
        (A) LENGTH: 318 amino acids
        (B) TYPE: amino acid
        (D) TOPOLOGY: linear (xi) SEQUENCE DESCRIPTION: SEQ ID NO: 32

```
Leu Gly Lys Ala Gly Ser Val Val Trp Met Leu Cys Ala Ile Trp Val
                 5                  10                  15

Ala Ala Asp Ala Leu Thr Val Glu Thr Thr Gln Asp Ile Leu Arg Ala
                20                  25                  30

Ala Arg Gly Arg Ser Val Thr Leu Pro Cys Thr Tyr Asn Thr Tyr Val
                35                  40                  45

Ser Asp Arg Glu Gly Phe Ile Gln Trp Asp Lys Leu Leu Arg Ser Gln
                50                  55                  60

Thr Glu Arg Val Val Thr Trp Asn Phe Val Thr Lys Lys Tyr Ile Tyr
65                  70                  75                  80

Gly Asn Arg Tyr Glu Asn Arg Val Arg Val Ser Asn Asp Ala Glu Leu
                85                  90                  95
```

```
Ser Asn Ala Ser Ile Thr Ile Asp Gln Leu Thr Met Asp Asp Asn Gly
                100                 105                 110

Thr Tyr Glu Cys Ser Val Ser Leu Met Ser Asp Gln Asp Val Asn Ala
            115                 120                 125

Lys Ser Arg Val Arg Leu Leu Val Leu Val Pro Pro Ser Lys Pro Asp
        130                 135                 140

Cys Ser Ile Gln Gly Glu Met Val Ile Gly Asn Asn Ile Gln Leu Thr
145                 150                 155                 160

Cys His Ser Ala Glu Gly Ser Pro Ser Pro Gln Tyr Ser Trp Lys Ser
                165                 170                 175

Tyr Asn Ala Gln Asn Gln Gln Arg Pro Leu Thr Gln Pro Val Ser Gly
            180                 185                 190

Glu Pro Leu Leu Leu Lys Asn Ile Ser Thr Glu Thr Ala Gly Tyr Tyr
        195                 200                 205

Ile Cys Thr Ser Ser Asn Asp Val Gly Ile Glu Ser Cys Asn Ile Thr
210                 215                 220

Val Ala Pro Arg Pro Pro Ser Met Asn Ile Ala Leu Tyr Ala Gly Ile
225                 230                 235                 240

Ala Gly Ser Val Phe Val Ala Leu Ile Ile Ile Gly Val Ile Val Tyr
                245                 250                 255

Cys Cys Cys Cys Arg Glu Lys Asp Asp Lys Asp Gln Asp Arg Glu Asp
            260                 265                 270

Ala Arg Pro Asn Arg Ala Ala Tyr Gln Val Pro Lys Lys Glu Gln Lys
        275                 280                 285

Glu Ile Ser Arg Gly Arg Glu Asp Glu Asp Asp His Arg His Glu Asp
290                 295                 300

Arg Trp Ser Ser Gly Arg Ser Thr Pro Asp Gln Pro Phe Gln
305                 310                 315
```

(2) INFORMATION FOR SEQ ID NO: 33:

(i) SEQUENCE CHARACTERISTICS:
        (A) LENGTH: 2803 nucleotides
        (B) TYPE: nucleic acid
        (C) STRANDEDNESS: single
        (D) TOPOLOGY: linear (xi) SEQUENCE DESCRIPTION: SEQ ID NO: 33:

```
CTACCCCTTT GTGAGCAGTC TAGGACTTTG TACACCTGTT AAGTAGGGAG           50

AAGGCAGGGG AGGTGGCTGG TTTAAGGGGA ACTTGAGGGA AGTAGGGAAG          100

ACTCCTCTTG GGACCTTTGG AGTAGGTGAC ACATGAGCCC AGCCCCAGCT          150

CACCTGCCAA TCCAGCTGAG GAGCTCACCT GCCAATCCAG CTGAGGCTGG          200

GCAGAGGTGG GTGAGAAGAG GGAAAATTGC AGGGACCTCC AGTTGGGCCA          250

GGCCAGAAGC TGCTGTAGCT TTAACCAGAC AGCTCAGACC TGTCTGGAGG          300

CTGCCAGTGA CAGGTTAGGT TTAGGGCAGA GAAGAAGCAA GACCATGGTG          350

GGGAAGATGT GGCCTGTGTT GTGGACACTC TGTGCAGTCA GGGTGACCGT          400

CGATGCCATC TCTGTGGAAA CTCCGCAGGA CGTTCTTCGG GCTTCGCAGG          450

GAAAGAGTGT CACCCTGCCC TGCACCTACC ACACTTCCAC CTCCAGTCGA          500

GAGGGACTTA TTCAATGGGA TAAGCTCCTC CTCACTCATA CGGAAAGGGT          550

GGTCATCTGG CCGTTTTCAA ACAAAAACTA CATCCATGGT GAGCTTTATA          600

AGAATCGCGT CAGCATATCC AACAATGCTG AGCAGTCCGA TGCCTCCATC          650
```

-continued

```
ACCATTGATC AGCTGACCAT GGCTGACAAC GGCACCTACG AGTGTTCTGT       700

CTCGCTGATG TCAGACCTGG AGGGCAACAC CAAGTCACGT GTCCGCCTGT       750

TGGTCCTCGT GCCACCCTCC AAACCAGAAT GCGGCATCGA GGGAGAGACC       800

ATAATTGGGA ACAACATCCA GCTGACCTGC CAATCAAAGG AGGGCTCACC       850

AACCCCTCAG TACAGCTGGA AGAGGTACAA CATCCTGAAT CAGGAGCAGC       900

CCCTGGCCCA GCCAGCCTCA GGTCAGCCTG TCTCCCTGAA GAATATCTCC       950

ACAGACACAT CGGGTTACTA CATCTGTACC TCCAGCAATG AGGAGGGGAC      1000

GCAGTTCTGC AACATCACGG TGGCCGTCAG ATCTCCCTCC ATGAACGTGG      1050

CCCTGTATGT GGGCATCGCG GTGGGCGTGG TTGCAGCCCT CATTATCATT      1100

GGCATCATCA TCTACTGCTG CTGCTGCCGA GGGAAGGACG ACAACACTGA      1150

AGACAAGGAG GATGCAAGGC CGAACCGGGA AGCCTATGAG GAGCCACCAG      1200

AGCAGCTAAG AGAACTTTCC AGAGAGAGGG AGGAGGAGGA TGACTACAGG      1250

CAAGAAGAGC AGAGGAGCAC TGGGCGTGAA TCCCCGGACC ACCTCGACCA      1300

GTGACAGGCC AGCAGCAGAG GGCGGCGGAG GAAGGGTTAG GGGTTCATTC      1350

TCCCGCTTCC TGGCCTCCCT TCTCCTTTCT AAGCCCTGTT CTCCTGTCCC      1400

TCCATCCCAG ACATTGATGG GGACATTTCT TCCCCAGTGT CAGCTGTGGG      1450

GAACATGGCT GGCCTGGTAA GGGGGTCCCT GTGCTGATCC TGCTGACCTC      1500

ACTGTCCTGT GAAGTAACCC CTCCTGGCTG TGACACCTGG TGCGGGCCTG      1550

GCCCTCACTC AAGACCAGGC TGCAGCCTCC ACTTCCCTCG TAGTTGGCAG      1600

GAGCTCCTGG AAGCACAGCG CTGAGCATGG GGCGCTCCCA CTCAGAACTC      1650

TCCAGGGAGG CGATGCCAGC CTTGGGGGGT GGGGCTGTC CTGCTCACCT      1700

GTGTGCCCAG CACCTGGAGG GGCACCAGGT GGAGGGTTTG CACTCCACAC      1750

ATCTTTCTTG AATGAATGAA AGAATAAGTG AGTATGCTTG GGCCCTGCAT      1800

TGGCCTGGCC TCCAGCTCCC ACTCCCTTTC CAACCTCACT TCCCGTAGCT      1850

GCCAGTATGT TCCAAACCCT CCTGGGAAGG CCACCTCCCA CTCCTGCTGC      1900

ACAGGCCCTG GGGAGCTTTT GCCCACACAC TTTCCATCTC TGCCTGTCAA      1950

TATCGTACCT GTCCCTCCAG GCCCATCTCA AATCACAAGG ATTTCTCTAA      2000

CCCTATCCTA ATTGTCCACA TACGTGGAAA CAATCCTGTT ACTCTGTCCC      2050

ACGTCCAATC ATGGGCCACA AGGCACAGTC TTCTGAGCGA GTGCTCTCAC      2100

TGTATTAGAG CGCCAGCTCC TTGGGGCAGG GCCTGGGCCT CATGGCTTTT      2150

GCTTTCCCTG AAGCCCTAGT AGCTGGCGCC CATCCTAGTG GGCACTTAAG      2200

CTTAATTGGG GAAACTGCTT TGATTGGTTG TGCCTTCCCT TCTCTGGTCT      2250

CCTTGAGATG ATCGTAGACA CAGGGATGAT TCCCACCCAA ACCCACGTAT      2300

TCATTCAGTG AGTAAACAC GAATTGATTT AAAGTGAACA CACACAAGGG      2350

AGCTTGCTTG CAGATGGTCT GAGTTCTTGT GTCCTGGTAA TTCCTCTCCA      2400

GGCCAGAATA ATTGGCATGT CTCCTCAACC CACATGGGGT TCCTGGTTGT      2450

TCCTGCATCC CGATACCTCA GCCCTGGCCC TGCCCAGCCC ATTTGGGCTC      2500

TGGTTTTCTG GTGGGGCTGT CCTGCTGCCC TCCCACAGCC TCCTTCTGTT      2550

TGTCGAGCAT TTCTTCTACT CTTGAGAGCT CAGGCAGCGT TAGGGCTGCT      2600

TAGGTCTCAT GGACCAGTGG CTGGTCTCAC CCAACTGCAG TTTACTATTG      2650
```

-continued

| | |
|---|---|
| CTATCTTTTC TGGATGATCA GAAAAATAAT TCCATAAATC TATTGTCTAC | 2700 |
| TTGCGATTTT TTAAAAAATG TATATTTTTA TATATATTGT TAAATCCTTT | 2750 |
| GCTTCATTCC AAATGCTTTC AGTAATAATA AAATTGTGGG TGGAAAAAAA | 2800 |
| AAA | 2803 |

What is claimed is:

1. Isolated nucleic acid molecule which encodes the protein portion of a protein containing molecule which binds to monoclonal antibody A33, wherein the protein portion has a molecular weight of from 40–45 kD as determined by SDS-PAGE under non-reducing conditions.

2. The isolated nucleic acid molecule of claim 1, wherein said molecule has the nucleotide sequence set forth in SEQ ID NO: 23.

3. The isolated nucleic acid molecule of claim 1, wherein said A33 protein has the amino acid sequence set forth in SEQ ID NO: 22 or an amino acid sequence consisting of amino acids 22–319 of SEQ ID NO: 22.

4. Expression vector comprising the isolated nucleic acid molecule of claim 1 operably linked to a promoter.

5. A host cell transformed or transfected with the nucleic acid molecule of claim 1.

6. A host cell transformed or transfected with the expression vector of claim 4.

* * * * *